(12) United States Patent
David et al.

(10) Patent No.: US 6,816,603 B2
(45) Date of Patent: Nov. 9, 2004

(54) METHOD AND APPARATUS FOR REMOTE MEDICAL MONITORING INCORPORATING VIDEO PROCESSING AND SYSTEM OF MOTOR TASKS

(75) Inventors: Daniel David, Ranana (IL); Zipora David, Wilmette, IL (US); Mark Mikhlin, Yehud (IL); Avmir Margolis, Hertzlya (IL); Semion Garber, Givataim (IL)

(73) Assignee: Commwell, Inc., Evanston, IL (US)

( * ) Notice: Subject to any disclaimer, the term of this patent is extended or adjusted under 35 U.S.C. 154(b) by 0 days.

(21) Appl. No.: 10/276,465

(22) PCT Filed: May 18, 2001

(86) PCT No.: PCT/US01/16180
§ 371 (c)(1),
(2), (4) Date: Nov. 18, 2002

(87) PCT Pub. No.: WO01/88836
PCT Pub. Date: Nov. 22, 2001

(65) Prior Publication Data
US 2003/0228033 A1 Dec. 11, 2003

Related U.S. Application Data

(60) Provisional application No. 60/205,186, filed on May 18, 2000, and provisional application No. 60/205,279, filed on May 18, 2000.

(51) Int. Cl.$^7$ .................................................. G06K 9/00
(52) U.S. Cl. ...................... 382/107; 382/174; 600/301
(58) Field of Search ................................ 382/104, 103, 382/107, 218, 251, 38, 174, 190; 340/904, 907, 933; 348/113, 154; 356/313, 27; 353/80; 73/488; 600/301

(56) References Cited

U.S. PATENT DOCUMENTS

| | | | | |
|---|---|---|---|---|
| 4,457,599 A | * | 7/1984 | Sawicki ........................ 352/89 |
| 4,779,095 A | * | 10/1988 | Guerreri ...................... 340/904 |
| 5,441,047 A | * | 8/1995 | David et al. ................. 600/483 |
| 5,469,536 A | * | 11/1995 | Blank .......................... 345/594 |
| 5,483,601 A | * | 1/1996 | Faulkner ..................... 382/115 |
| 5,621,825 A | * | 4/1997 | Masaki et al. .............. 382/274 |
| 5,625,410 A | * | 4/1997 | Washino et al. ............ 348/154 |
| 5,781,165 A | * | 7/1998 | Tabata ........................... 345/8 |
| 5,812,193 A | * | 9/1998 | Tomitaka et al. ........... 348/369 |
| 5,854,856 A | * | 12/1998 | Moura et al. ............... 382/232 |
| 5,980,429 A | | 11/1999 | Nashner et al. |
| 6,288,753 B1 | * | 9/2001 | DeNicola et al. ........... 348/586 |
| 6,323,776 B1 | * | 11/2001 | Jackson et al. ............. 340/679 |
| 6,352,517 B1 | * | 3/2002 | Flock et al. ................. 600/595 |
| 6,645,147 B1 | * | 11/2003 | Jackson et al. ............. 600/458 |

* cited by examiner

Primary Examiner—Bhavesh M. Mehta
Assistant Examiner—Barry Choobin
(74) Attorney, Agent, or Firm—Banner & Witcoff, Ltd.

(57) ABSTRACT

Video image data is received in the form of a sequence of images representative of a subject performing one or more predetermined tasks within a new environment (FIG. 3 element 31). A plurality of silhouettes is generated from the video image data and combined to provide a motion portrait (FIG. 6). Motion characteristics are then calculated based on the motion portrait and may be compared with normal or previous motion characteristics as part of diagnostic analysis (38).

27 Claims, 15 Drawing Sheets

Restricted Right Knee

| Parameter | Unit | Right Value | Right StDev | Left Value | Left StDev |
|---|---|---|---|---|---|
| — Temporal parameter of the Stride — | | | | | |
| Cycle | frames | 29.88 | 0.61 | | |
| Velocity | pxl/fd | 4.49 | 0.1 | | |
| Double Sup | frames | 4.31 | 0.56 | 2.88 | 0.35 |
| Single Sup | frames | 10.27 | 0.44 | 12.42 | 0.61 |
| Middle Sing | - | 0.44 | 0.03 | 0.47 | 0.03 |
| — Spatial parameter of the Stride — | | | | | |
| Step Length | pixel X | 123.6 | 8.25 | 135.1 | 17.64 |
| Advances | pixel X | 138.25 | 7.84 | 134.78 | 23.59 |
| Step Width | pixel X | 6.08 | 2.06 | 5.35 | 4.73 |
| Foot Length | pixel X | 59.62 | 1.26 | 58.54 | 2.83 |
| — Foot-Floor angle projection at: — | | | | | |
| Initial Cont | degrees | 17.62 | 2.5 | 17.42 | 4.24 |
| Mid Single | degrees | 2.15 | 1.41 | 1.12 | 3.54 |
| Push Off | degrees | -38.62 | 5.45 | -.21 | 4.24 |
| After I.C. | degrees | 12.69 | 2.39 | 7.23 | 4.24 |
| Before I.C. | degrees | 19.92 | 2.69 | 20.04 | 4.95 |

Normal Walking

| Parameter | Unit | Right Value | Right StDev | Left Value | Left StDev |
|---|---|---|---|---|---|
| — Temporal parameter of the Stride — | | | | | |
| Cycle | frames | 29.79 | 0.37 | | |
| Velocity | pxl/fd | 5.32 | 0.12 | | |
| Double Sup | frames | 4.14 | 0.41 | 3.68 | 0.25 |
| Single Sup | frames | 10.96 | 0.37 | 11 | 0 |
| Middle Sing | - | 0.46 | 0.03 | 0.5 | 0 |
| — Spatial parameter of the Stride — | | | | | |
| Step Length | pixel X | 162.21 | 4.88 | 161.58 | 5.31 |
| Advances | pixel X | 162.4 | 5.76 | 161.67 | 4.91 |
| Step Width | pixel X | 3.98 | 2.32 | 2.15 | 1.65 |
| Foot Length | pixel X | 59.14 | 1.17 | 58.07 | 0.92 |
| — Foot-Floor angle projection at: — | | | | | |
| Initial Cont | degrees | 22.64 | 2.92 | 23.21 | 3.7 |
| Mid Single | degrees | 0.14 | 1.51 | 0.43 | 1.02 |
| Push Off | degrees | -38.86 | 3.57 | -44.29 | 3.22 |
| After I.C. | degrees | 11 | 1.96 | 14.07 | 1.59 |
| Before I.C. | degrees | 26.93 | 3.43 | 26.79 | 3.21 |

Figure 15

METHOD AND APPARATUS FOR REMOTE MEDICAL MONITORING INCORPORATING VIDEO PROCESSING AND SYSTEM OF MOTOR TASKS

CROSS REFERENCE TO RELATED APPLICATIONS

Related subject matter is found in U.S. Pat. No. 5,441,047, and U.S. Pat. No. 5,544,649, the teachings of which patents are hereby incorporated by this reference. Additional related subject matter is found in U.S. Provisional Patent Application Serial No. 60/205,186 filed May 18, 2000 entitled "Method And Apparatus For Facilitating Medical Pre-Screening" assigned to the same assignee of the present invention and U.S. Provisional Patent Application Serial No. 60/205,279 entitled Method and Apparatus for Remote Medical Monitoring Incorporating Video Processing and System of Motor Tasks filed May 18, 2000, assigned to the same assignee, incorporated herewith by reference and for which priority is claimed.

TECHNICAL FIELD

The present invention relates to techniques for monitoring the medical condition of a subject or subject/patient most especially neuromuscular motor activity, and, to a method and apparatus for monitoring a subject or subject/patient at a remote site from a central station by means of interactive visual, audio and data transmission communications. While the invention is also suitable for use in any situation where any subject or subject/patient is to be monitored at a site remote from a central station, an important application is the monitoring and caring for the elderly (both well and ill persons) in the home environment. Thus, the present invention can also be said to relate to the field of geriatric care. Further, the techniques disclosed may also be utilized in a hospital or clinic setting inasmuch as they constitute diagnostic techniques useful for any person and at any local or remote location. Additionally the techniques and methods have application to other disciplines including, but not limited to, psychological diagnosis and monitoring, and interrogation monitoring and analysis. Finally, the invention enables conduct of physiological analysis utilizing a single video camera and without markers.

BACKGROUND OF THE INVENTION

Ambulatory Care in General

Most of the resources for modern medicine have been invested in the development of highly sophisticated hospital facilities. Therefore, institutional patient care has become prohibitively expensive, in many cases overused and for a substantial number of patients potentially harmful. The tendency to substitute costly institutional patient care with effective and cost containing extra-institutional, ambulatory medical facilities is gaining rapid momentum. These attempts however are still confined to the delivery of care in outpatient clinics to which the patient has to come to obtain medical care, or home nurse visits which are short, scarce, and insufficient. The combination of growing sophistication in ambulatory monitoring technology together with the explosive development of telecommunication provides the ideal substrate to enable the development of highly sophisticated, reliable and affordable, remotely controlled, remote monitoring capabilities which can monitor, analyze and assess many physiological parameters in any potential subject and in any possible location. Such a system is specially suited to provide a sophisticated platform or home care facilities for a wide spectrum of subject/patient.

The described invention is a neuromuscular and motor activity remote monitoring system for any person in need of remote assessment of physiological, psychological, and other parameters. From the subject/patient care aspect one of the important applications of this system is monitoring and care of the elderly geriatric population. This is due to the complexity of the holistic approach to geriatric care, which will be elaborated below.

Geriatric Ambulatory Home Monitoring

Modern society with its improvement in living conditions and advanced health care has brought about a marked prolongation of life expectancy. This change has resulted in a dramatic and progressive increase in the geriatric population. A large percentage of the geriatric population needs continuous general, as well as medical, supervision and care. For example, supervision of daily activities such as dressing, personal hygiene, eating and safety as well as supervision of their health status is necessary. Furthermore, the relief of loneliness and anxiety is a major, yet unsolved, problem to be addressed. These and other facets of the management of the ever increasing geriatric population have yet to be successfully addressed and solved.

The creation of retirement facilities and old age homes, as well as other geriatric facilities, provide only a partial solution to the problems facing the geriatric population. The geriatric population, a constantly increasing fraction of society, has become increasingly dependent upon the delivery of home health and general care, which has its own set of challenges and drawbacks.

The notion of ambulatory (home environment) subject/patient care is gaining increased popularity and importance. This shift in subject/patient care from the "sheltered" institutional milieu to the subject/patient's home, work place, or recreational environment is due primarily to a radical change in concepts. That is, specialists in geriatric care now tend to keep the aged in their own natural environment for as long as possible.

Except for scarce model organizations, home care is still carried out either by the subject/patient's family or by nonprofessional help, or, in the usual circumstance, by professional, highly trained personnel at very significant expense. The monitoring equipment at home care facilities is usually minimal or nonexistent, and the subject/patient has to be transported to the doctor's office or other diagnostic facility to allow proper evaluation and treatment.

Subject/patient follow-up is presently done by means of home visits of nurses which are of sporadic nature, time consuming and generally very expensive. A visiting nurse can perform about 5–6 home visits per day. The visits have to be short and can usually not be carried out on a daily basis. Moreover, a visiting nurse program provides no facilities for continuous monitoring of the subject/patient and thus no sophisticated care, except in fortuitous circumstances, in times of emergency. The remainder of day after the visiting nurse has left is often a period of isolation and loneliness for the subject/patient. The existing home care nursing facilities divert skilled nurses, a scarce commodity, from the hospital environment and uses them in a highly inefficient manner due to the wide dispersion of the subject/patients and the lack of sophisticated diagnostic facilities in the subject/patient's home. Clearly, the practice of visiting nurses leaves much to be desired.

These considerations apply to the general population as well, as the spiraling cost of hospital care has lead to a dramatic increase in the use of outpatient care as a treatment modality.

Falls and Injuries in the Aged

Additional facts support development of an improved home health care system especially for a geriatric population. In particular, falls are a major health problem among the elderly, causing injury, disability and death. One third (some studies suggest half) of those over the age of 65 suffer at least one fall each year. The rate of falling increases to 40% among those who exceed the age of 80. According to the National Safety Council, falls accounted for one-third of the death total for the elderly. Those who survive falls may have restricted activity, soft-tissue injuries, or fractures. It is estimated that up to 5% of falls by elderly persons result in fractures. A similar percent result in soft-tissue injury requiring hospitalization or immobilization for an extended period. It is estimated that hip fractures resulting from falls cost approximately $2 billion in the United States during 1980. Falls are mentioned as a contributing factor to admissions to nursing homes.

The factors leading to falls can be divided into two main groups: environmental factors and medical factors. In spite of the difficulty in the surveillance of subject/patient condition before a fall, almost all researchers share the conclusion that environmental hazards are decreasingly important in causing falls as age increases. A clear correlation between clinical or medical problems and the incident of falls by the elderly has been established. Many of these medical problems of the elderly or infirm can be detected by simple clinical observation. For example gait and balance abnormality may indicate difficulty with neurologic and musculoskeletal functions that may contribute to physical instability. Changes in gait can be identified by the following: slow speed, short step length, narrow stride width, wide range of stepping frequency, a large variability of step length, and increasing variability with increasing frequency.

Thus, there are relatively straightforward techniques that enable diagnosis of a predisposition or likelihood of falls among the elderly. U.S. Pat. Nos. 5,441,047 and 5,544,649 ("the '047 and '649 patents") disclose inexpensive procedures for undertaking such diagnoses or investigating such predispositions in a large subject/patient population wherein the kinematic condition of the subject/patient can be investigated or where the appearance, and reflex activity of the subject/patient can be investigated with ease. In particular, the '047 and '649 patents describe an ambulatory (in the home) subject/patient health monitoring system wherein a health care worker at a central station monitors the subject/patient, while the subject/patient is at a remote location. The subject/patient may be a person having a specific medical condition being monitored or may be an elderly person desiring general medical surveillance in the home environment. Video transmission cameras are provided at the subject/patient's remote location and at the central station such that the subject/patient and the health care worker are in interactive visual and audio communication. A communications network such as an interactive cable television is used for this purpose. Various medical condition sensing and monitoring equipment are placed in the subject/patient's home, depending on the particular medical needs of the subject/patient. The subject/patient's medical condition is measured or sensed in the home and the resulting data is transmitted to the central station for analysis and display. The health care worker then is placed into interactive visual communication with the subject/patient concerning the subject/patient's general well being, as well as the subject/patient's medical condition. Thus, the health care worker can make "home visits" electronically, twenty-four hours a day, seven days a week in a non-intrusive, cost effective, privacy protecting manner.

Prior Art Testing Techniques

While the '047 and '649 patents (incorporated herewith by reference) represent an improvement over prior art techniques, additional testing methods are needed to properly and fully exploit the opportunities provided by remote diagnostic systems as well as hospital or clinic site diagnosis. The common approach to functional testing of the motor ability of elderly persons is based on scoring the performance of complex functional tests such as "Get Up and Go", "Fregley Ataxia Test Battery" and others. The resulting score is used for estimating the risk of falling, mainly, for purposes of epidemiological studies. Each test consists of a set of simple motor tasks. For clinical decision-making, physicians generally take into account the results of the separate tasks, instead of the resulting score of the whole test. It is known that the ability to perform a simple motion task is directly connected with concrete medical conditions of a subject/patient whereas the resulting score only provides a general impression. These tests very often require special equipment (e.g., static and dynamic force plates with or without feedback, markers on specific body locations, and 6 to 10 meters of walkway etc.). Moreover these tests require the presence of an assistant to guide the test and insure the accuracy and safety of its performance. As a rule, such testing can only be realized in a clinic that has the required equipment and a sufficiently skilled staff. Likewise, such testing is too expensive for everyday practice, usually cannot be repeated as often as necessary and therefore cannot be used to perform thorough monitoring of elderly subject/patients with restricted capacities to visit clinics.

U.S. Pat. No. 5,980,429 ("the '429 patent") describes a monitoring technique for training programs where effectiveness of training is assessed through a thorough comparison of quantitative and qualitative measured parameters with quantitative and qualitative benchmark data. Qualitative parameters relate to the accuracy of performing the tasks and quantitative parameters to a number of successive performances in a certain period of training. To obtain a sequence of qualitative benchmark data, training tasks are arranged by level of difficulty of performance. The measured results of a given task are categorized according to the completeness and accuracy of its performance. Thus a system for objective assessment is realized. Benchmark data are defined from previous subject's performances or from data derived from corresponding reference groups. The "Sew Balance Master" test for assessment of motor and balance ability of a subject/patient described in the '429 patent is a typical example of a well-designed clinical test. The training program is intended for persons with an intact central nervous system, i.e., can only be applied in specific injuries. Moreover, the assessment always relates to a person that does his hardest exercises on his own highest level. Hence the arrangement of the motor tasks by degree of difficulty may be adequate even if the accuracy of the assessment is restricted by dividing the results of measurements over 3 to 5 categories.

However, an elderly subject performing tasks in accordance with such testing schemes, without any assistant, will mostly carry out the tasks on a far lower level than his or her maximum abilities. So, the tasks should be designed with a degree of difficulty but free from essential muscle tension and unstable poses that could lead to a fall. Moreover, nervous and physiological disorders, often present in elderly persons, necessitate individual tailoring of the difficulty level of the tests. Taking into account the fact that in elderly persons many essential disorders, associated with motor difficulties, evolve very gradually, the monitoring system should be able to detect small trend changes in motor behavior of the subject/patient.

Thus, it can be seen that techniques leveraging the availability of video image data, i.e., that build upon and improve the teachings of the '047 and '649 patents, would be an important advancement of the art. Furthermore, testing methodologies, including testing contents and protocols should take advantage of these advances, thereby maintaining and improving the diagnostic reliability of current medical techniques.

SUMMARY OF THE INVENTION

The present invention is directed to improvements to the interactive video and audio subject/patient monitoring system disclosed in the '047 and '649 patents by providing a video processing technique whereby motion characteristics are readily discerned from video image data of a subject/patient. (The term "subject/patient" as used herein is to be interpreted broadly to include elderly persons, persons actively being treated or monitored for specific medical ailments, as well as persons who need to have their general medical condition and gait and balance status monitored by practitioners for any reason, for example: astronauts in space stations etc. Additionally, persons who are being monitored for psychological condition, mood, truth telling and general physical condition are considered subject/patients. By way of example, but not limitation, interrogation techniques which rely upon physical response to evince truthfulness or falsehood may utilize variations of the techniques disclosed herein along and in combination with other physical response measurements such as respiration, heart rate, etc.) Furthermore, the present invention sets forth a system of motor tasks and protocols for their execution that is particularly adapted for use in the interactive television and audio monitoring system as well as being useful at a hospital or clinic site where clinicians work directly with subject/patients or any other remote monitoring scenario. An example of a series of diagnostic tests is disclosed wherein the tests are susceptible of qualitative, quantitative and/or image processing review and analysis. The term "medical" herein is broadly inclusive of physical, psychological and behavior conditions by way of example.

The image processing techniques enable diagnosis associated with skeletal and muscular movement in a highly quantitative and recordable manner. Thus, the video image of the patient performing each of the tasks in the protocol is captured by a video acquisition system. The video image data is received in the form of a sequence of equally spaced (in the time domain) images. The acquired images are then compressed using standard image compression techniques such as that defined by MJPEG compressed images in order to reduce the data content to allow storage on a local disk or to allow transmission to a remote location. Unlike neuromuscular motor activity measured in standard gait and balance laboratories which require a multitude of cameras and require that markers be placed on the patient, the present invention, without limiting it, produces adequate results with the use of a single camera and without the use of markers.

A pre-processing element follows the image acquisition. The purpose of the preprocessing element is to remove the background and produce a sequence of silhouette images or outline images of the patient on a frame-by-frame or field-by-field basis by applying a sequence of standard image processing operations on the acquired images. The image processing operations, well known in the art, include contrast control, brightness control, segmentation and edge detection. The pre-processing sequence of operations may be manually defined by an operator of the system or automatically discovered through the use of quality indicators and feedback to search for the best set of operations.

The pre-processing may be performed at the central location or at the remote location in a distributed system. The result of the pre-processing is a plurality of matrices (one per frame or field of the original video image sequence) containing the silhouette or outline image. In the case where the pre-processing is performed at the patient location, the resultant pre-processed file is transferred to the central facility for continued post processing.

A post-processing element follows the pre-processing. The purpose of the post-processing is to make measurements of various parameters of the silhouette or outline of the patient on a frame-by-frame or field-by-field basis. The aforementioned parameters or mathematical combinations of these parameters represent physiological indices associated with gait and balance as with other neuromuscular motor activities. An example of a measured parameter in the space domain is the maximum height that a patient's foot is raised from the floor. An example of a measured parameter in the time domain is the time it takes a patient to complete a cycle while walking.

The results of the measurements from the post-processing are stored for long-term to monitoring and trending. The system provides for the definition of predefined normal value ranges for the results as well as adaptive individual normal value ranges based on the historical data from a particular patient An alarm notification is provided when a value falls outside the expected normal range.

A graphical "finger print" of the patients walking pattern is obtained by summing the is individual matrices provided from the output of the pre-processing and storing the result in a resultant matrix. This is similar to placing each outline from a single frame onto a transparency and placing the transparencies one on top of the other. The resulting picture provides a unique characteristic template of the patient that may be analyzed and compared to previously stored templates of the patient. Changes from the normal historical pattern represent changes in the neuromuscular motor activity of the patient that may be indicative of physiological problems.

An integral part of this invention is the protocols used to test the patient. Each protocol is an action or a plurality of actions that the patient must perform. Some of the protocols such as walking in a straight line or walking in place produce direct physiological protocols produce the indirect physiological information such as the ability to complete a sequence of balance tasks each of which are subsequently more difficult resulting in a numerical grade. The combined tests are designed to elicit all necessary physical and neurological information relating to a patient's ability to perform neuromuscular motor tasks. The tasks are particularly chosen to maximize safety and to minimize the probability of the patient falling down or otherwise losing balance when performing the tasks. To this end, tasks are preferably ordered by difficulty within certain tests. The level of difficulty associated with the said task thereby offers an inherent qualitative measure. This qualitative information quantized by the degree of difficulty is stored together with other quantitative results. The use of degree of difficulty has particular relevance in rehabilitation.

These and other advantages and features of the subject invention will become apparent from the detailed description of the invention that follows.

BRIEF DESCRIPTION OF THE DRAWING

In the detailed description of presently preferred embodiments of the present invention which follows, reference will be made to the drawings comprised of the following Figures, wherein like reference numerals refer to like elements in the various views and wherein:

FIG. 15 is an exemplary report showing the values obtained from one test based on walking in a straight line.

DETAILED DESCRIPTION OF THE INVENTION

A. General Description of System Hardware

Figure 1:
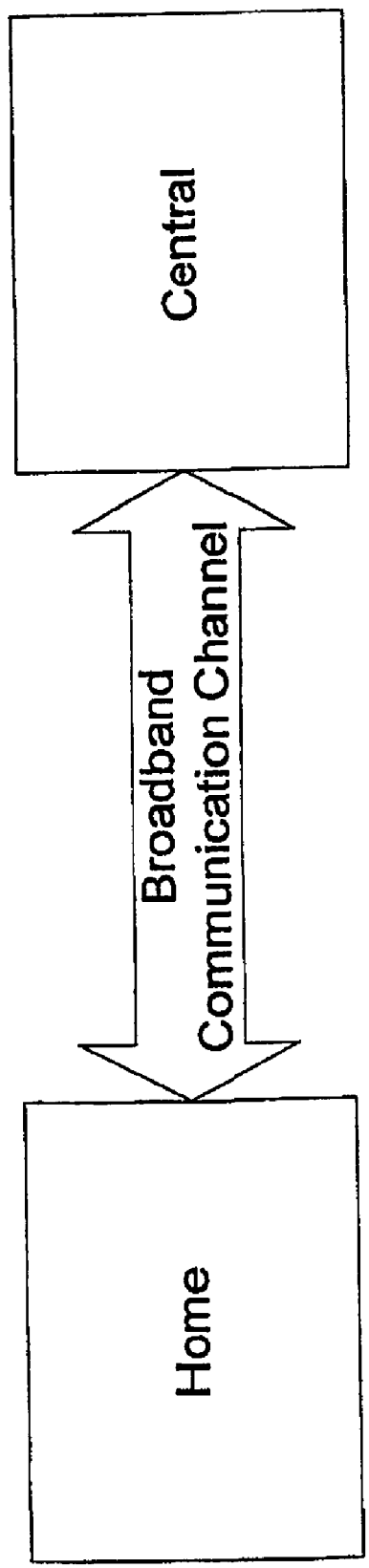
FIG. 1 is a simplified, overall functional block diagram of the system

The system of the present invention consists of two distinct entities FIG. 1, one is a subject/patient unit, located in the area where the subject/patient performs the measurement, this unit is also typically referred to as the home unit 11 since it is placed in the home of the subject/patient in one of the preferred embodiments and a second entity, a central unit 12 located in the area where the medical practitioner administrates the conduction of the measurements and analyzes the results. The two entities are connected via a wideband communication channel 13. This configuration allows for the central unit to be separated from the home unit. It also allows for a single central unit to communicate either serially or simultaneously with more than one home unit. In both of these instances a public carrier provides the communication channel where the Internet is one of the possible means of communications. The configuration also allows for local use such as in a clinic or hospital where the communication channel may be a local area network. It further allows for very remote use such as the possible to communicate between a ground control and an orbiting space shuttle.

The system of the present invention uses or incorporates relatively inexpensive home medical monitoring equipment that includes one or more cameras. When used as part of a home monitoring system it may include additional sensors and measuring devices for the particular physiological/medical parameters to be monitored. The subject/patient's remote location/home equipment is simple to use and modular to allow for the accommodation of the monitoring device to the specific needs of each subject/patient. To reduce production costs and to avoid complex maintenance problems, the remote home unit includes the absolutely needed components of the measuring device while most of the sophisticated elements are located in the central unit. The raw data, including video image data, is transmitted to the central station, which includes all of the needed sophistication to allow for the storage, transformation, display and interpretation of the data. The need for expensive equipment in the remote location/home is thus avoided.

The central station includes a computer-based multi-channel data analysis and display unit that enables the interpretation, display, and storage of the transmitted data. This central station is preferably equipped with alarm mechanisms to alert the staff to any aberration from the expected. The central station further includes apparatus for the communication of data to all authorities involved in the wide spectrum of the subject/patient's needs, e.g., emergency care agencies, the subject/patient's physicians, nursing services, social workers, etc.

The central station is preferably provided with the capability of automatically scanning predesignated subject/patient remote/home units at predetermined intervals to provide continuous supervision of specific parameters. In some instances, the central station may monitor continuously one or more parameters, e.g., ECG, blood pressure, respiration, etc. The embodiment disclosed enables one highly trained nurse or subject/patient-monitoring personnel located at the control center to supervise and monitor as many as 50 subject/patients either seriatim or substantially simultaneously. Whereas a visiting nurse may only be able to visit 5 or 6 homes per day in person, a nurse at the central station may be able to visit 5 or 6 subject/patients per hour by making electronic "home visits".

Any broadband communication system is suitable for the bi-directional real time contact with the subject/patient in the remote location/home. One such medium is cable television that provides an already existing, widespread and highly suitable system via cable modems for interactive visual communication with most residential units in densely populated urban areas. The ambulatory subject/patient monitoring system integrating the latest advances in biomedical technology with cable television or any other available and suitable communication system provide safe and accurate general and medical supervision for the geriatric/homebound population in their own, natural environment.

It will be appreciated that as advances in telecommunications develop, other techniques for transmission of video signals between a central station and the home may be desirable and economically feasible. For example, satellite and radio transmission of the video signal and/or monitored medical data, or transmission via modem through the telephone lines, may also prove satisfactory. In due time the system will possible using the internet or similar computer networks as it's main communication system both for the data transmission to and from the remote location/home as well as the use of the database by other authorities such as physicians insurers, government agencies, etc.

Figure 2:
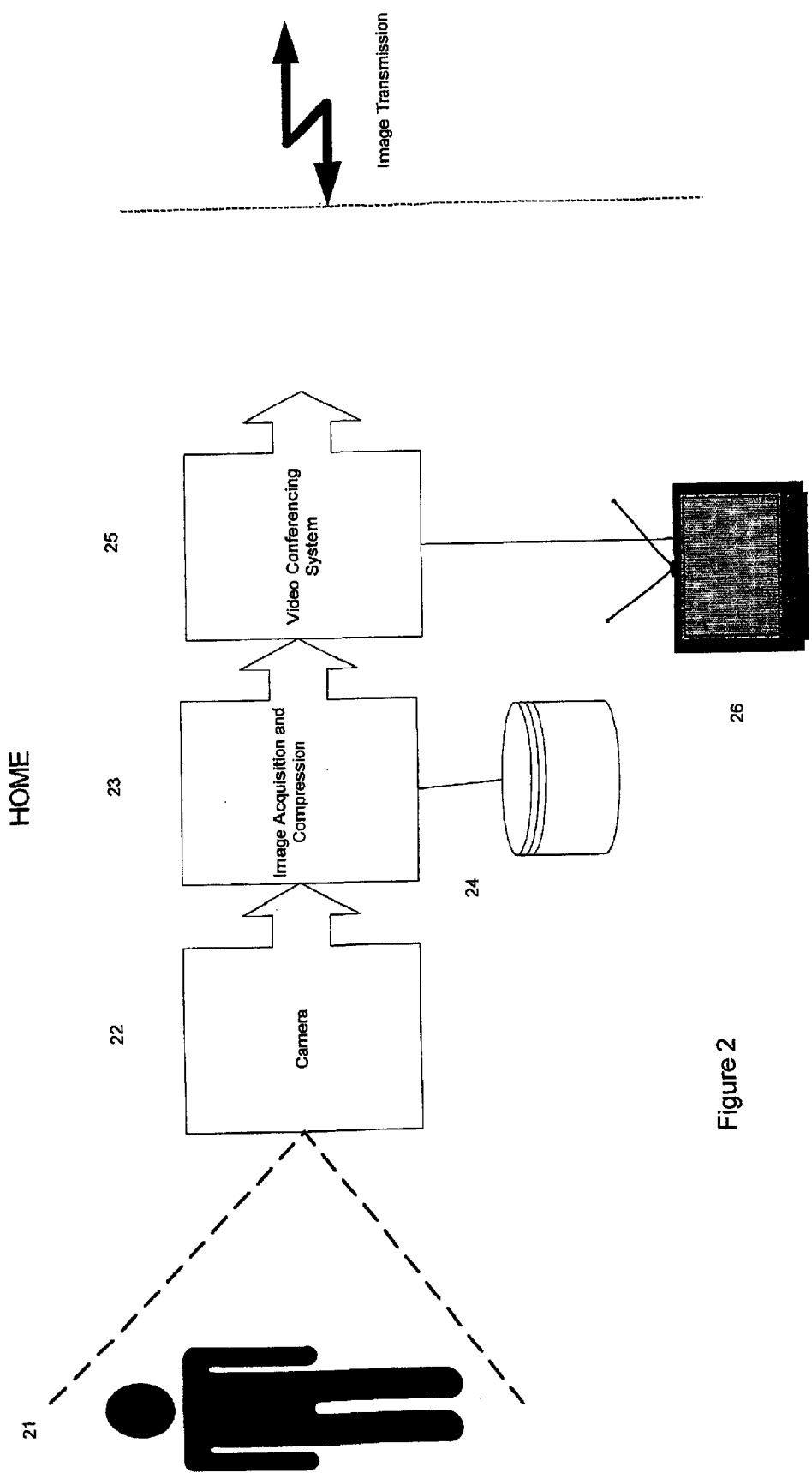
FIG. 2 is a schematic diagram illustrating one possible configuration of the home system

A typical embodiment of the home system is shown in FIG. 2. A single camera 22 is used to take a motion picture video of the subject/patient 21. The camera has a wide angle and provides for remote control from the central station for pan, tilt, zoom as well as other controls such as brightness and contrast. Typically the camera will provide 30 frames per second and transmit composites or supervideo signal in NTSC standard to the video acquisition 23. The video acquisition will acquire the analog video signal and convert it to a digital Y Cr and Cb values. The Y Cr and Cb values are then passed through a video compression component that compresses the video. The compressed video may be locally stored in a disk 24 for later transmission, this is necessary in the case that the desired communication bandwidth is not appropriate to transfer the compressed video in realtime or directly transferred as part of an integrated videoconferencing system 25. In addition the integrated videoconferencing system 25 provides for interactive audio-visual interactions with the central station so that the subject/patient may see and speak with the medical practitioner on the home TV set 26 and the medical practitioner may see the subject/patient on the center monitor. The interactive communication is an important aspect of the system in that it allows for the medical practitioner to instruct the subject/patient to perform the testing and to monitor the subject/patient while the tests are being performed. It should be noted that the video quality required for monitoring the subject/patient may be less than the video quality required for the automated neuromuscular motor analysis of the patient. Video conferencing may be performed using either standard H.323 compression or using more proprietary compression techniques such as wavelet compression. The audio signal may be digitized and received and transmitted in either a compressed or non-compressed format. Should the video be stored locally as a file on disk 24, it would transmitted to the central station as a file using common communication transfer protocols such as TCP/IP to insure integrity. The acquisition, storage and videoconferencing may be implemented using a standard PC, in this case the various elements are implemented as PCBs which reside on the bus of the PC. The control program and the video conferencing application run under the operating system of the PC. An alternative implementation would be to use an embedded system with a microprocessor and DSP to perform the acquisition, compression and video-conferencing functions. Communications is provided by an interface to a standard communication modem. This may be a cable modem, xDSL, ISDN or other broadband communication modem.

Figure 3:
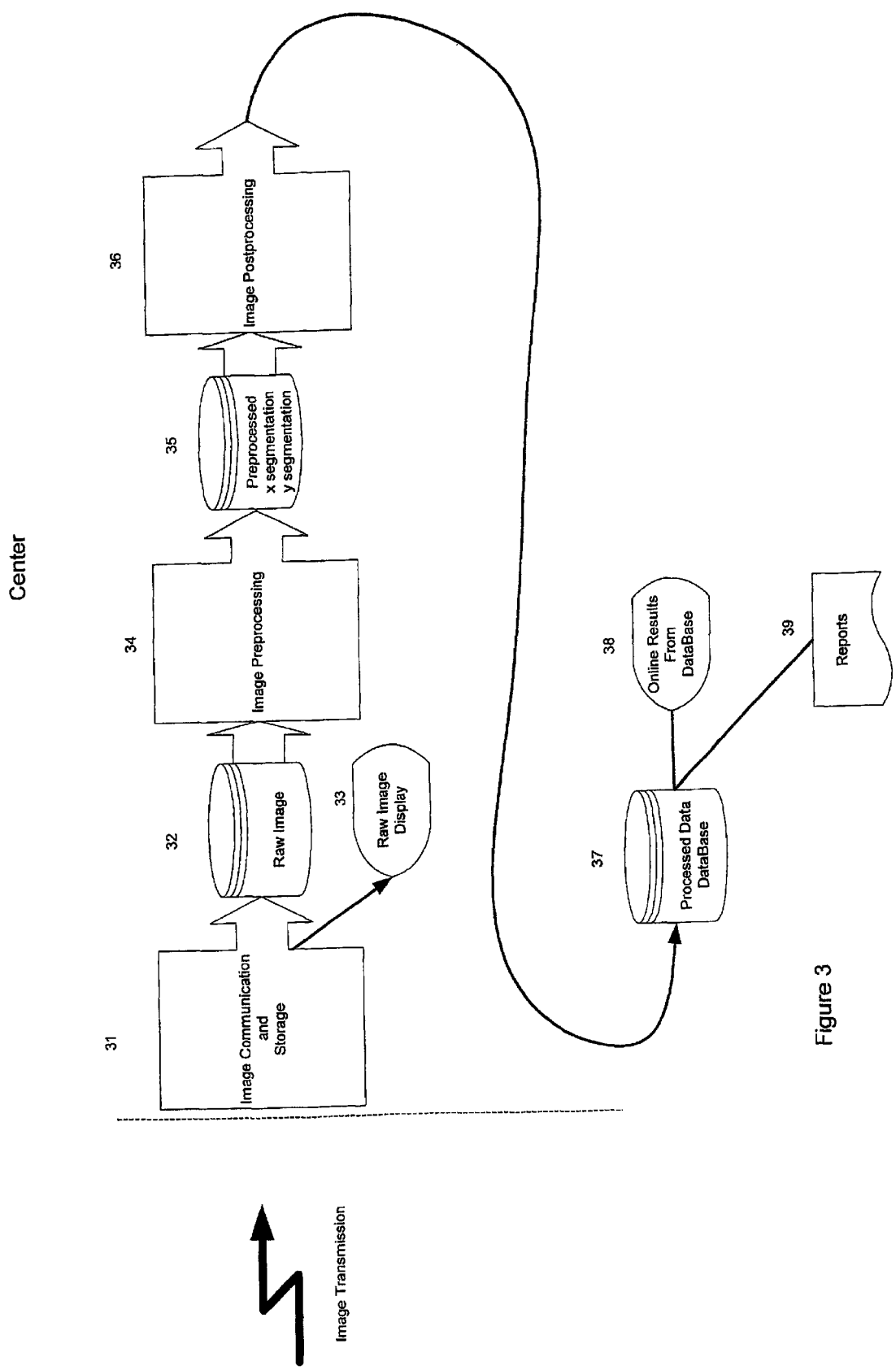
FIG. 3 is a schematic diagram illustrating one possible configuration of the central station.

A typical embodiment of the nurse station is shown in FIG. 3. Images arrive into the central station from the communication system 31 and are stored on a local disk 32. This element also provides for video-conferencing with the home system. The online images are seen in a window on the local display 33. Images stored on the local disk 32 are then preprocessed by a preprocessing application 34. The preprocessing application removes background information, obtains an outline or silhouette of the subject/patient on a frame by frame or field by field bases and performs x and y segmentation of the images. The results of the preprocessing are stored in an x and y segmentation file of the image 35. The x and y segmentation files may be used to obtain a fingerprint of the image figure xx or may be used for post processing 36. Post processing transforms the results of the x and y segmentation to meaningful quantitative and qualitative information as a function of the specific test which was performed. Post processing are the set of algorithms used to extract the desired data for the x and y segmentation and to perform the necessary manipulation of this data based on the features which are desired to extract from the data. The post processed data is stored in a data base 37 together with other patient information. This data becomes part of the historical record of the patient and may be used to compare present data with past data, trigger alarms as seen on a display window 38 when any parameter resides outside the expected range and be used by reporting applications 39. Owing to the fact that the data resides in a database the data may be queried by other application programs which may run either on the local system or on a remote system which communicates with the data base. An example of the latter is a system running at a doctors office which may monitor the results of a particular patient.

B. Hospital or Clinic Analysis

While an important aspect of the described techniques is remote site monitoring, the protocols described hereinafter have significantly broader application and utility. That is, the described image monitoring may be conducted at any site including in hospital or at a clinic. In every circumstance, the images and other data are recorded, analyzed, stored or retained and compared with historic information or standard information. The practice of the described image processing and protocols at a hospital site will, for example, be a useful diagnostic tool for the medical practitioner. Thus, the described invention, though detailed in the context of remote monitoring, is equally applicable for on-site monitoring of subject/patient condition, both ill and well, and is an important diagnostic tool for on-site use.

The prevent invention utilizes a multifaceted approach to medical diagnosis relying upon the interactive technology heretofore described and the technology described in various co-pending applications. An important feature of such multifaceted diagnosis and a principal feature of the present invention, is video image processing of a patient to analyze gait, balance, skeletal condition, muscle condition and coordination and other physiological features and conditions. Briefly, video images of the outline of the body or a part of the body are recorded and analyzed either by a trained physician or nurse or by machine analysis in an effort to detect (a) a base line of performance or condition (2) variation from norms (3) changes over time (4) changes under stress, and (5) changes in emergency conditions. The imaging techniques may be utilized by themselves or in combination with other, diagnostic techniques, including traditional techniques, as well as test techniques described herein. The images are, in the system described, obtained by using video camera input signals obtained from the subject/patient location. However, the general techniques of image analysis are not restricted to such a monitoring system. Thus, they may be used, for example on site at a hospital.

C. Video Image Pre-Processing

Figure 4:
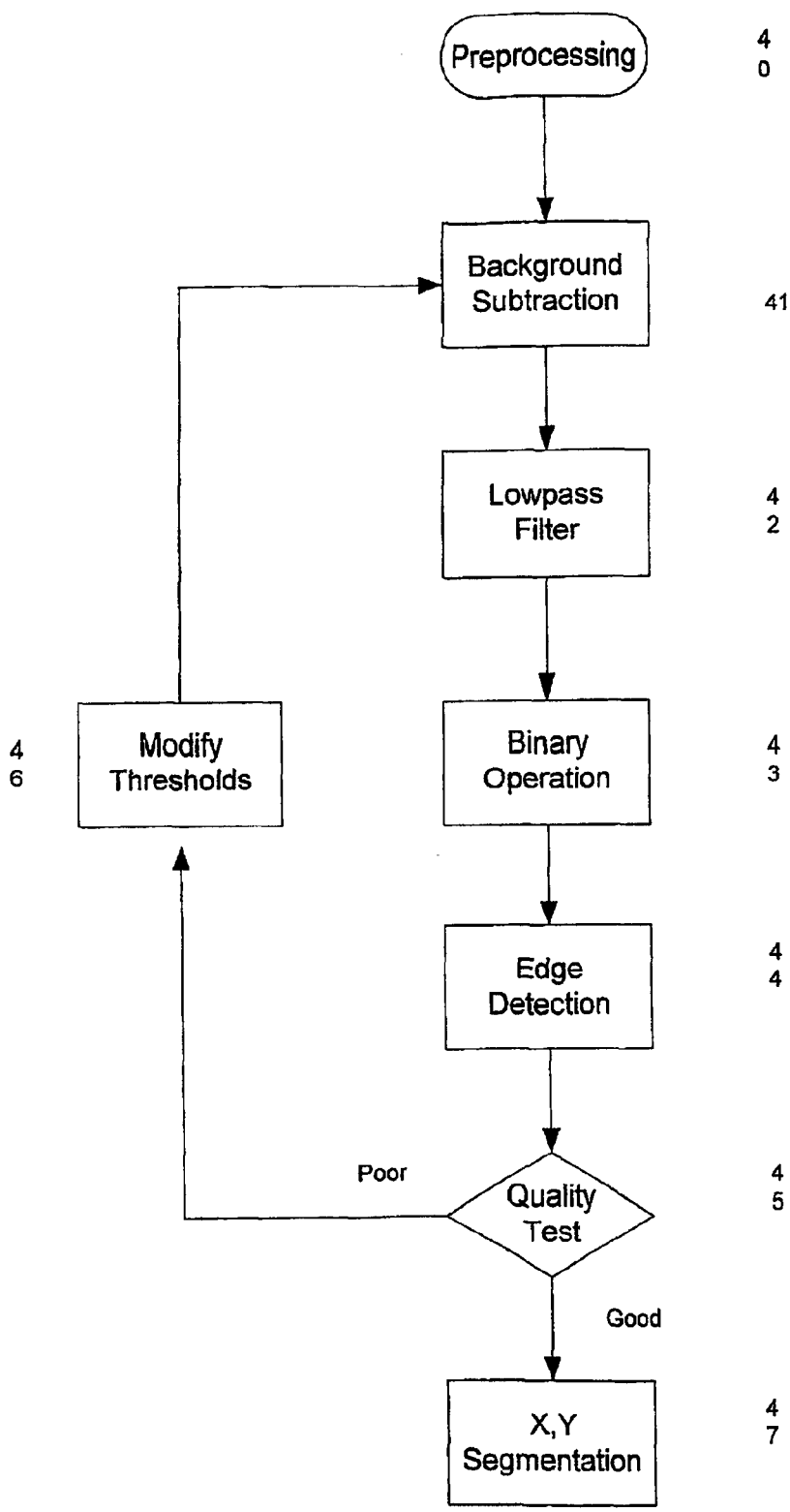
FIG. 4 is a flowchart illustrating a method for video image processing in accordance with the present invention.

Referring now to FIG. 4, there is illustrated, a system for performing video processing of images from a single video camera without markers on the subject in accordance with the present invention. In particular, FIG. 4 illustrates a preferred grouping of algorithms or subsystems 41–47. In one embodiment of the present invention, the system illustrated in FIG. 4 is implemented using PC or similar processing device executing software instructions stored in memory. Those having ordinary skill in the art will recognize that various implementations of the functionality described below, other than those illustrated in FIG. 4, are possible as a matter of design choice. Furthermore, implementations need not be restricted to a software implementations; for example, dedicated hardware devices may be used to implement certain portions of the functionality described below. Finally, the processing illustrated in FIG. 4 and described below is preferably carried out automatically upon reception of video image data. Alternatively, the video image data may be stored indefinitely, and the processing of FIG. 4 carried out only upon command.

Video image data from a single camera is received (via cable 31, for example) by a preprocessing subsystem 40.

Preferably, the video image data is color video data in a digitized and compressed format having a compression ratio of about 10. In practice, it is preferred that the camera 22 providing the video image data be positioned and fixed (so as to provide a static viewing area) at a location approximately 3 meters away from a gait path or other performance area to be used by the subject/patient. The pre-processing subsystem 40 performs conditioning steps necessary to place the video image data in a form suitable for continued processing. For example, the pre-processing may include, but is not limited to, noise suppression (smoothing) filters, and color preprocessing (brightness/contrast adjustment, histogram stretch, decreasing the number of used colors, i.e., bit-per-pixel). As one alternative, interlaced fields may be used, rather than frames. The video image data output 47 by the pre-processing subsystem 40 is essentially a series of digitized images of the subject/patient, preferably performing one or more tasks such as walking, etc.

Each frame output by the pre-processing subsystem 40 is provided to a quality subsystem 45 and a segmentation subsystem 47. The quality subsystem checks the quality of each image and modifies the various thresholds used in the processing if the quality is not acceptable.

Thus, prior to filming the subject/patient, an image of just the background alone, i.e., the area where the subject/patient is to be filmed, can be obtained by the system. This background-only image provides current background parameters. The calibration subsystem 46 then reads the environment parameters from a previous session for comparison with the current background parameters. Environment parameters include the color distribution model (illumination model) and camera parameters such as the lines or pixals, contrast sensitivity, etc. for a previous session. The environment parameters may also include a subject/patient's figure templates, i.e., data generally describing the subject/patient's dimensions and appearance. In the case where the previous and current environment parameters are very similar (as would be the case, for example, where the subject/patient always performs the testing at the same location), the successful video processing settings of the previous session are provided to the segmentation subsystem 47 for application to the image currently being processed. In the case of a new subject/patient or of essentially different previous and current environment parameters or inconsistent results of the test processing with the setting of the previous session, the processing parameters are chosen interactively applying varying combinations of processing tools to small portions of the images.

The parameters selected by the calibration subsystem 46 and the video image data from the pre-processing subsystem 41–45 are provided to the segmentation subsystem 47. In the context of the present invention, segmentation refers to the process of creating binary (i.e., all pixels are either black or white) or gray-scale (i.e., all pixels assume a value somewhere between the extremes of black and white) images of the subject/patient. To this end, a variety of techniques may be employed. One technique, edge detection processing, can be performed to discern the edge's of the subject/patient's image. For example, edge detection filters combined with thresholding (in which all values above a certain threshold are deemed black or white, and all values below the threshold are deemed the opposite) may be used. Alternatively, edge detection filters in combination with edge tracing as taught, for example, by S. M. Smith in "Reviews of Optic Flow, Motion Segmentation, Edge finding and Corner Finding". Techn. Report TR97SMS1, Oxford Centre for Functional Magnetic Resonance Imaging of the Brain (FMRIB) Department of Clinical Neurology, Oxford University, Oxford, UK, 1997, the teaching of which are incorporated herein by this reference.

Figure 8:
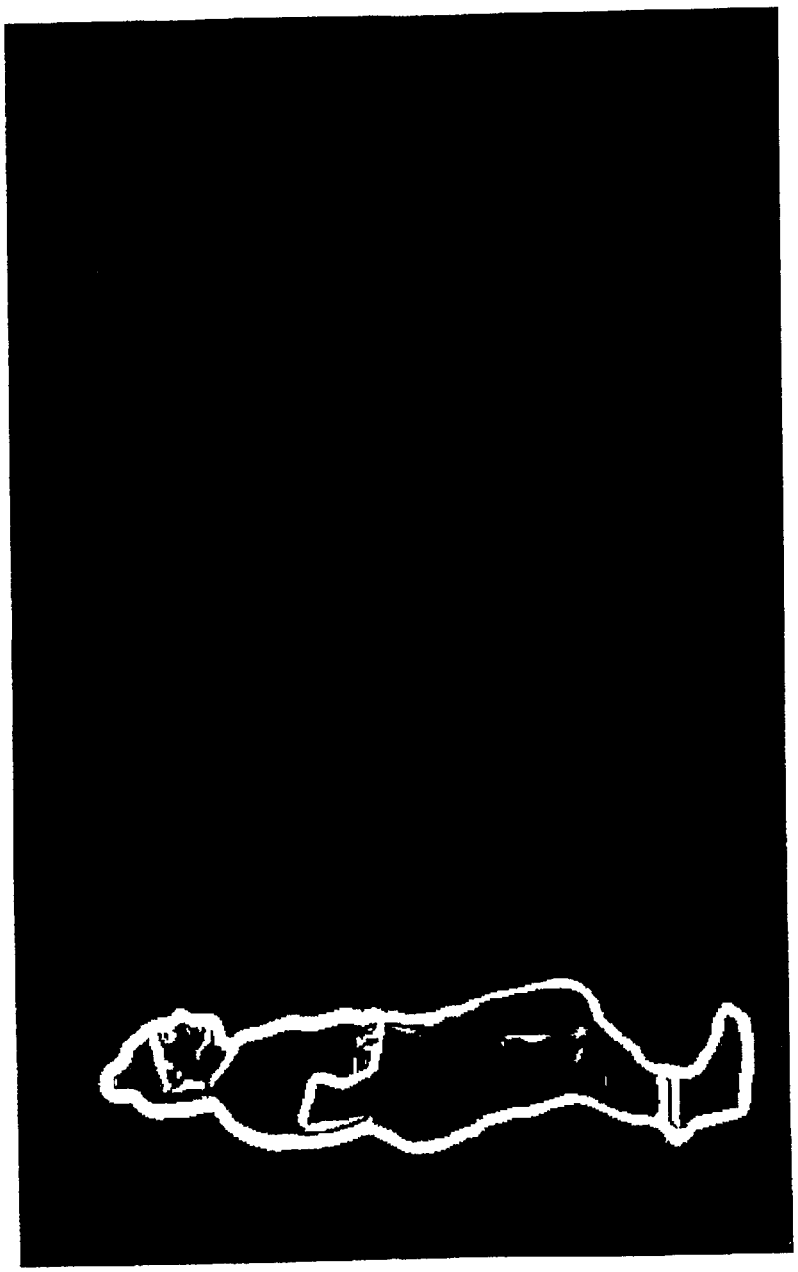
FIG. 8 is an exemplary x-silhouette in accordance with the present invention.

As noted above, background or environment parameters provided by the segmentation subsystem 47 may be used to subtract the background colors, leaving substantially little more than the subject/patient's image. Thus, the background parameters can be pixel color values, stored in a table, corresponding to various regions (preferably noncontiguous) within a given image. All pixels values in the image near or identical to the stored pixel values are then subtracted to remove the background content. In yet another alternative, the pixels of all images are first separated into a small number of groups according to features of images distinguishable by their color (using statistical criteria as taught, for example, by D. Comaniciu and P. Meer in "Robust Analysis of Feature Spaces: Color Image Segmentation", Techn. Report, Rutgers University, Piscataway N.J., 1997, the teachings of which are incorporated herein by this reference). Subsequently, the images are binarized using one of the above mentioned methods, e.g., edge detection and thresholding. Finally, combinations of the above techniques may be used. FIG. 8 illustrates an example of a binary image resulting from a color image in which the background content has been removed in accordance with the teachings above, and which has been passed through thresholding.

The binary or gray-scale images resulting from the binary processing 43 are provided to a boundary tracing subsystem 44 where the binary or gray-scale images are processed to provide only an outline or silhouette of the subject/patient in each image. In one embodiment, a so-called x-silhouette is used for this purpose. An x-silhouette comprises all points of a binary or gray-scale image lying at the leftmost and rightmost points lying on a horizontal line through any section of the subject/patient's figure.

Another alternative method for boundary tracing is to take a given image, with or without background subtraction, and shrink the image by a known factor, i.e., by a factor of 4 to 5 thus producing an image which is ¼ or ⅕ the size of the original image and resealed back up to the original size using the same factor. The result is a reduce resolution image. By subtracting the reduced resolution image from the original image, a good approximation of the subject/patient's boundary is provided. In one embodiment of the present invention, this technique is used periodically, i.e., every $5^{th}$, $10^{th}$, etc. image. The boundary thus generated is then used as an approximation to the subject/patient's figure boundary. All image processing and boundary tracing procedures are then performed in a relatively small neighborhood of this approximate boundary. Additionally, the approximations may be used as a basis, along with a complete silhouette, for interpolating points otherwise missing from incomplete silhouettes.

Figure 5:
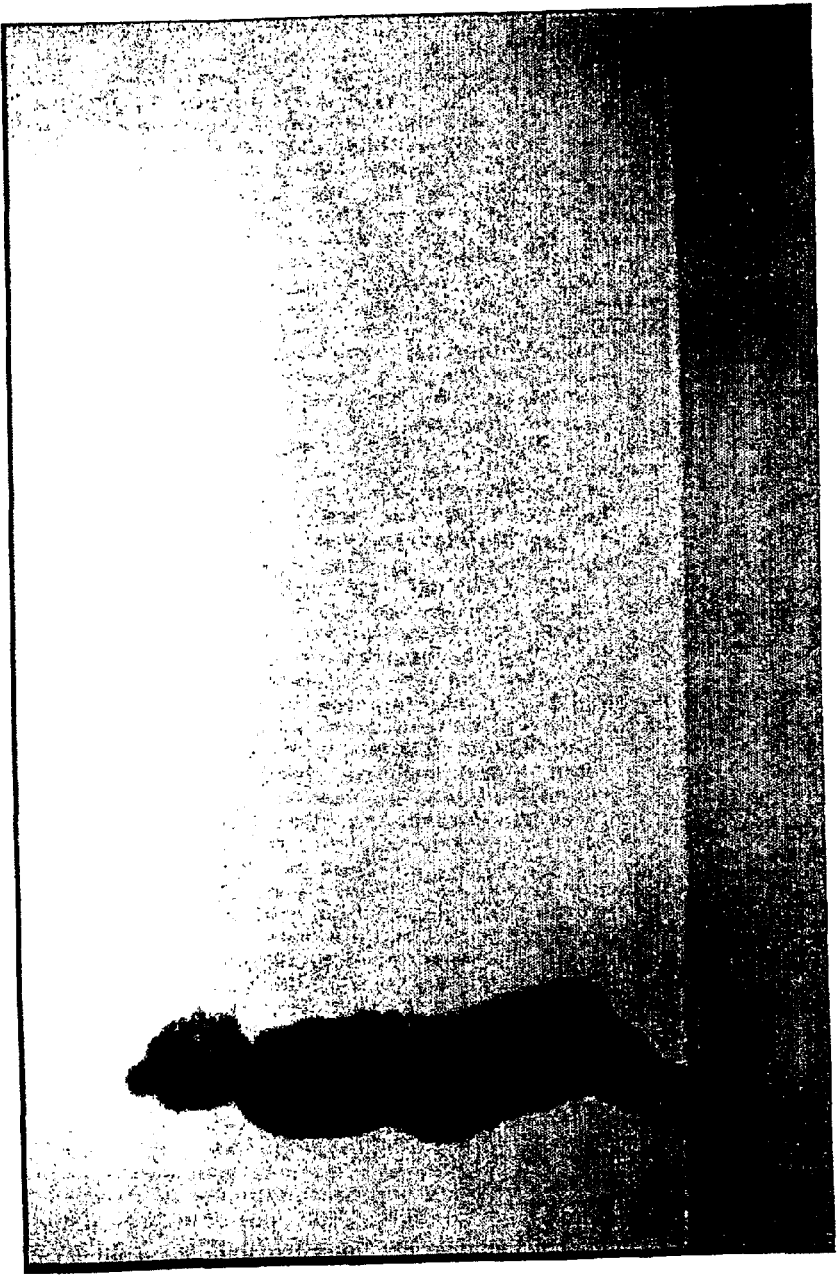
FIG. 5 is an exemplary raw video image prior to processing
Figure 6:
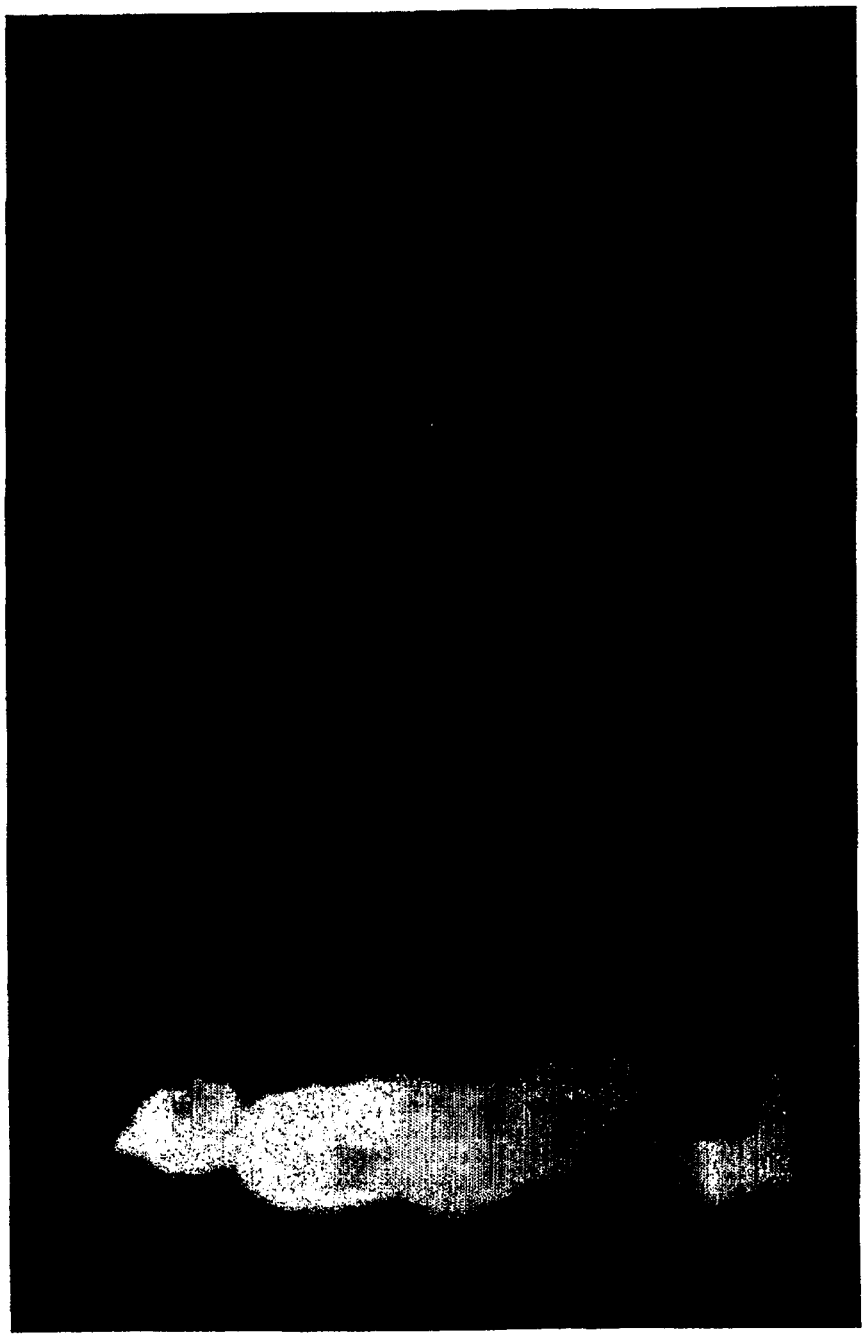
FIG. 6 is an exemplary image after background subtraction and filtering

The following is an example of the use of the above methods. A picture of the subject is shown in FIG. 5. The goal of the image processing is to remove the background and obtain a silhouette of the image. A second image exists in the system, taken without the subject in the picture. This image is referred to as the background image. The background is subtracted from the image of FIG. 5 on a pixel by pixel basis. This means essentially that if each pixel in a given frame is designated as an element of a matrix Pixel [FRAME,I,J] where the pixel located in the $I^{th}$ row and the $J^{th}$ column of the frame FRAME then the subtraction output is obtained by performing the subtraction of Pixel[FRAME, I,J]–Pixel[REFERENCE,I,J]. The result of the subtraction is then filtered using a low pass averaging 7×7 pixel filter. This operation produces the image seen in FIG. 6.

Figure 7:
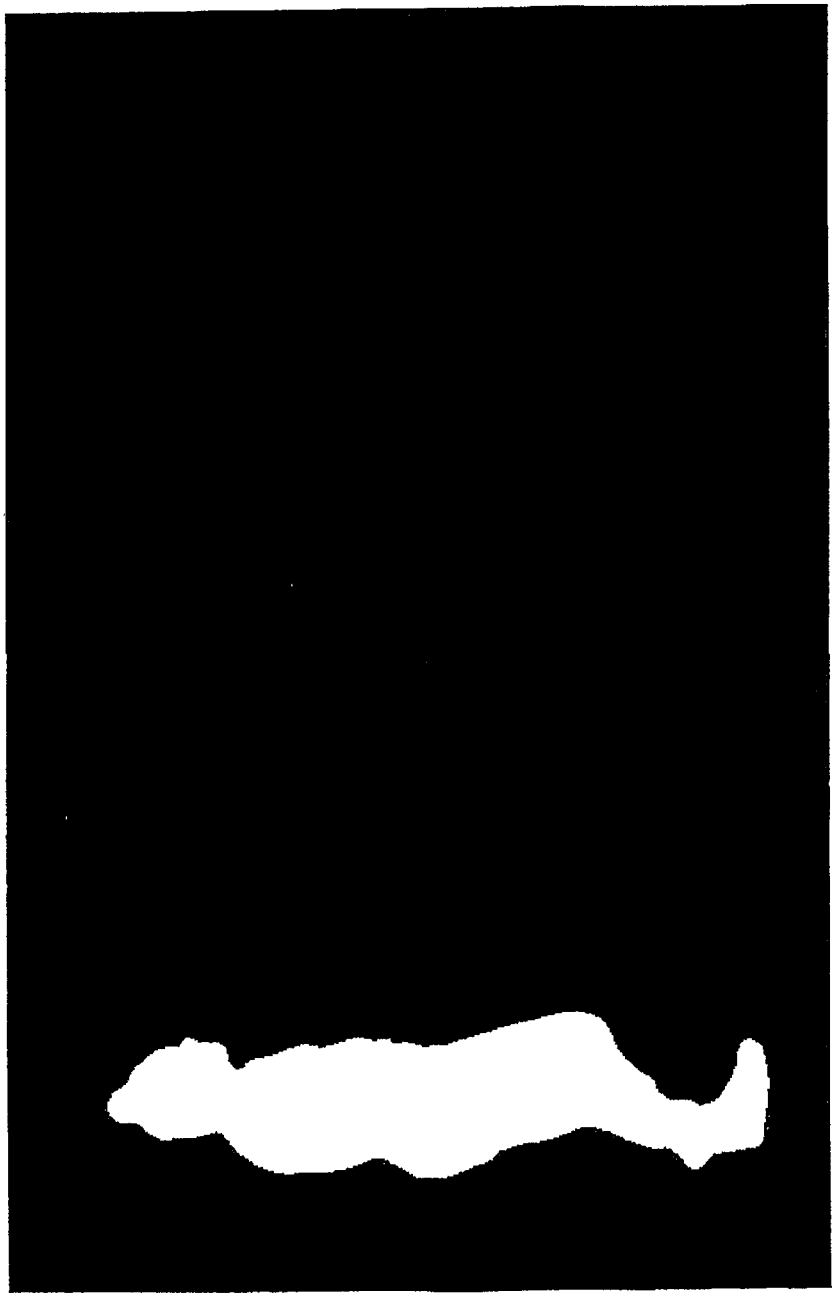
FIG. 7 is an exemplary binary image in accordance with the present invention.

The next step is to produce a binary image by setting a threshold such that all pixels values above the threshold are set to black and all values below the threshold are set to white, see FIG. 7. The next step is to perform edge detection on the binary image. The result of the edge detection is shown in FIG. 8. The output of edge detection is used to obtain couplets of data points in the x direction. The first member of the couplet is the start of the edge detected image in a given row and the second member of the couplet is the end of the edge detected image for the same row.

The matrix of couplets of the rows is referred to as the x segmentation matrix. A similar process is performed on each of the columns resulting in a y segmentation matrix. Further still, an x-segementation matrix, i.e. the matrix W indexed by a row index, j, and a frame index, k, is defined as:

$$W[j][k]=X_r[j][k]-X_l[j][k] \text{ for } j=1, 2, \ldots, N_{rows} \text{ and } k=1, \ldots, N_{frames} \quad \text{(Eq. 1)}$$

where $X_l[j][k]$ and $X_r[j][k]$ are the x-coordinates of the most left and right points respectively in the intersection of the subject/patient's figure on the i-th frame with the j-th row, $N_{rows}$ is the number of rows in a fixed rectangle containing the union of the subject/patient's figures in all frames, and $N_{frames}$ is the number of frames. Based on the x-segmentation matrix, left and right x-velocities and x-acceleration matrices, i.e. the matrices defined as the first and the second differences of the matrices $X_l[j][k]$ and $X_r[j][k]$ with respect to the k-th frame may also be defined.

D. Post Processing

Figure 9B:
FIGS. 9A and 9B are an exemplary motion portraits in accordance with the present invention.

One example of the use of the silhouettes, regardless of how they are produced, the silhouettes generated in this manner are combined as a pixel-wise conjunction or superposition of all silhouettes to provide a motion portrait. Stated another way, let Img[1], Img[2], . . . Img[N] be sequence of silhouettes generated as described above. The union of all Img[j] for j=1 to N is a motion portrait. An exemplary motion portrait, comprising a union of full silhouettes, is illustrated in FIG. 9. As shown, each of the black pixels corresponds to an object in motion. It is understood that motion portraits may be constructed from x-silhouettes, y-silhouettes or full silhouettes and, in one embodiment of the invention, motion portraits from each type of silhouette are provided.

Figure 9A:
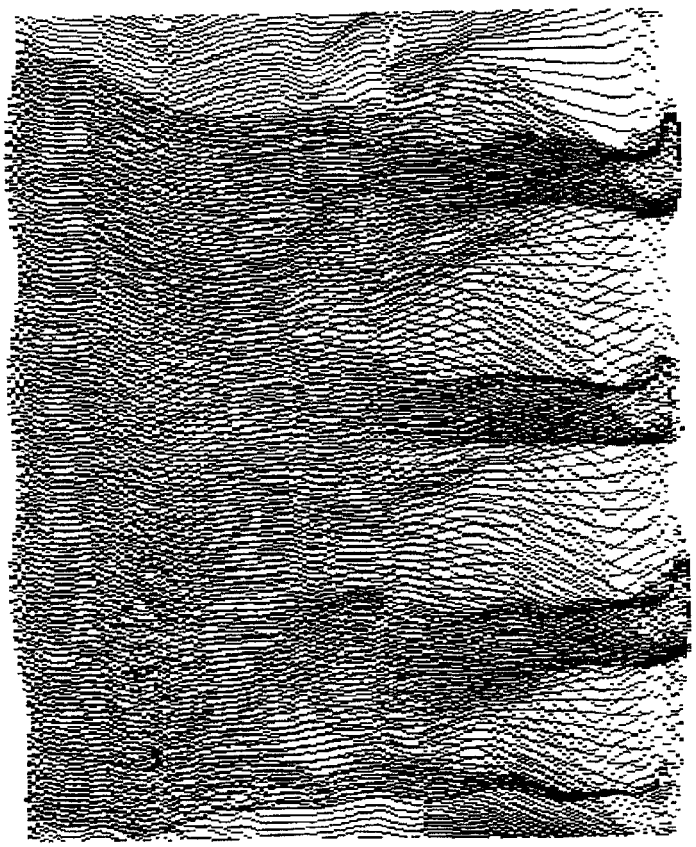

Depending on the condition of the subject/patient performing the tests, the motion portraits thus provided may be used to detect anomalies or other artifacts in the subject/patient's performance. For example, when a normal healthy subject/patient performs a gait test, the motion portrait will typically exhibit a smooth appearance in that the motion-based pixels will be evenly distributed throughout the motion portrait. On the other hand, for the same subject/patient walking with even a slight limp, the motion portrait will often be characterized by clusters of motion-based pixels with noticeable frequencies. Although such visual analysis of motion portraits can be used by skilled practitioners to detect various medical conditions, the present invention also provides for more analytical analysis of motion portraits. FIG. 9a shows a motion "finger print" of a normal walk, which can be easily distinguished from the motion finger print of an abnormal walk FIG. 9b.

Figure 10:
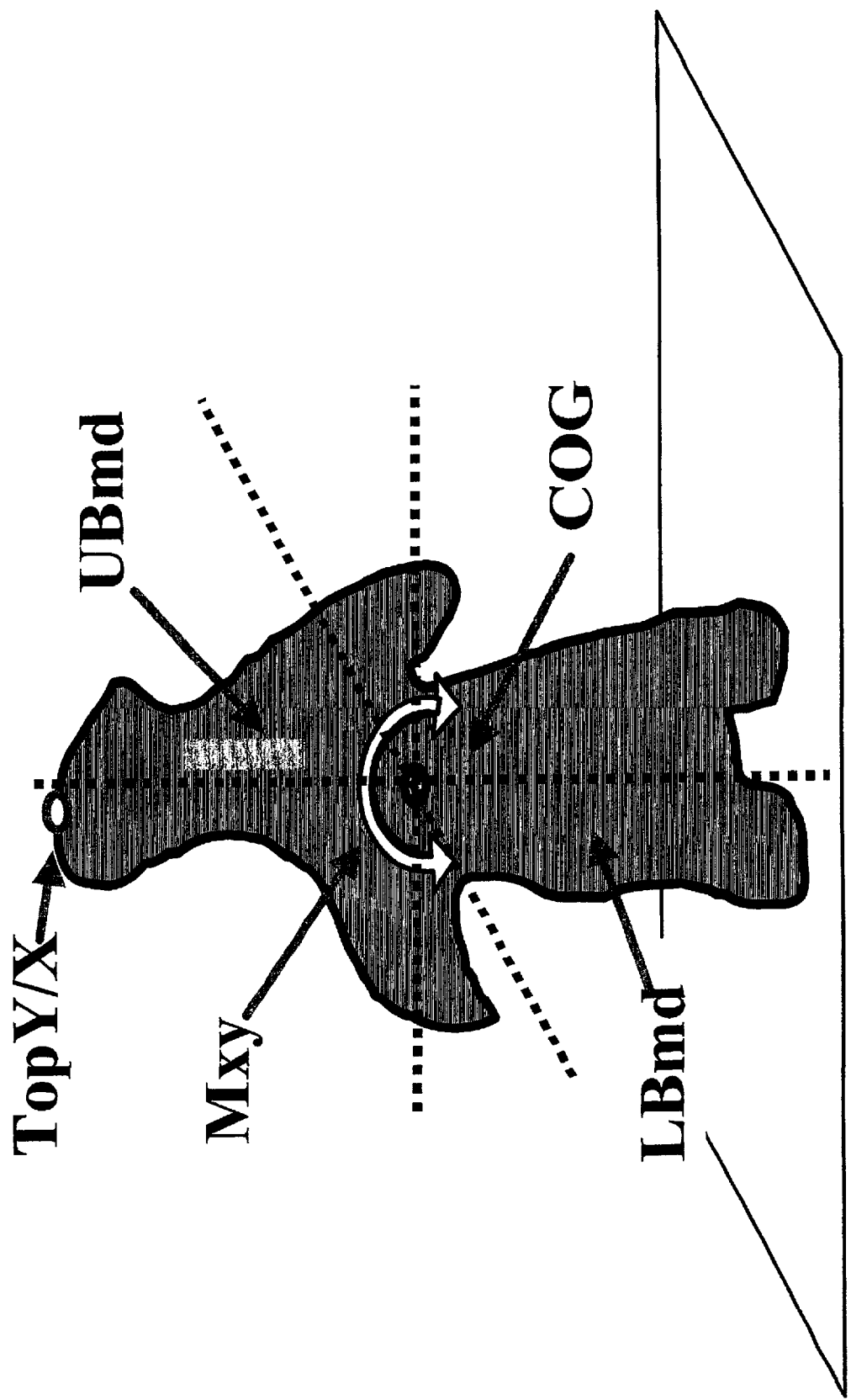
FIG. 10 is a drawing showing the various parameter measured from the segmentation data.

In particular, motion portraits can be processed by a motion characteristics calculation in the post processing stage. Generally, motion characteristics include any qualitative measurements that may be calculated based on the motion portraits. For example, discrete motion characteristics such as step length, the duration of carrying out of stages of motion tests, characteristic frequencies of the motion (especially, of the gait tests) can be calculated. Head motion characteristics (i.e., the slope, the top-point trajectory) or, more generally, trajectories of characteristic points of the subject/patient's figure (i.e., the center of gravity, knees, heels etc.) may also be directly calculated from the motion portrait data Typical data extracted from the x segmentation matrices, FIG. 10, are the coordinate values of the subject/patient summit, the extreme left and right points of the outline at the hands level, and the spectrum of the subject/patient's instant velocity on a frame by frame or field by field bases. Typical values from the y segmentation include timing (initial contact, push off and middle swing instances for both sides, the step width, and the sagittal projection of sole-floor angle at some instances for both sides. Other information include the silhouette area, the coordinates of the arbitrary center of mass of the silhouette. Since all of the silhouette outlines are defined for each frame or field and because each frame or field represents an inherent clock timing a graph can be made showing the various parameters and the subsequent changes in these parameters over time. The oscillations of the parameters obtained from the x segmentation have extremes that in normal walking strictly correspond to temporal parameters revealed from the foot-floor contact events.

Figure 11:
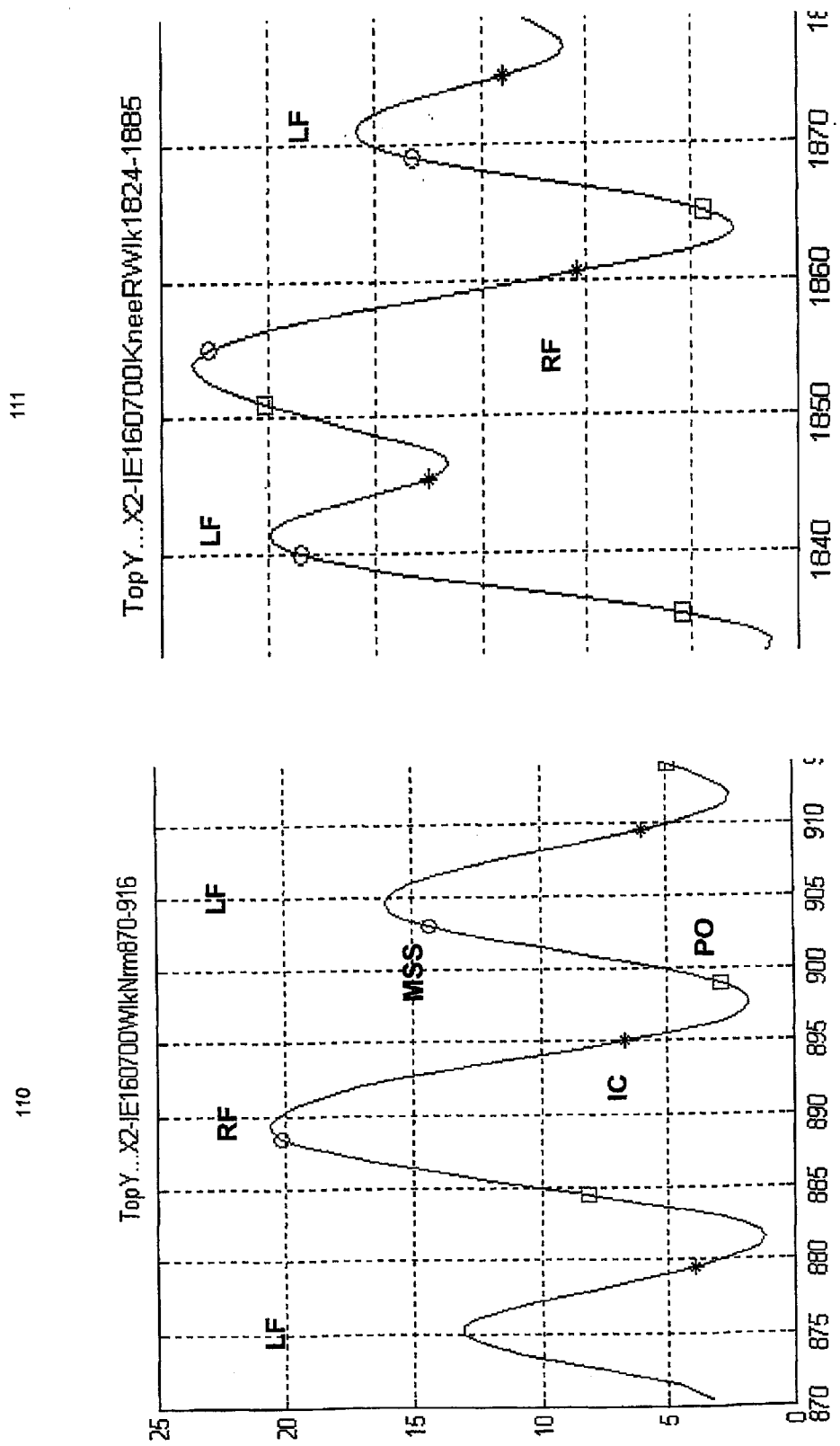
FIG. 11 is an exemplary graphical representation of the outcome of walking in a straight line.
Figure 12:
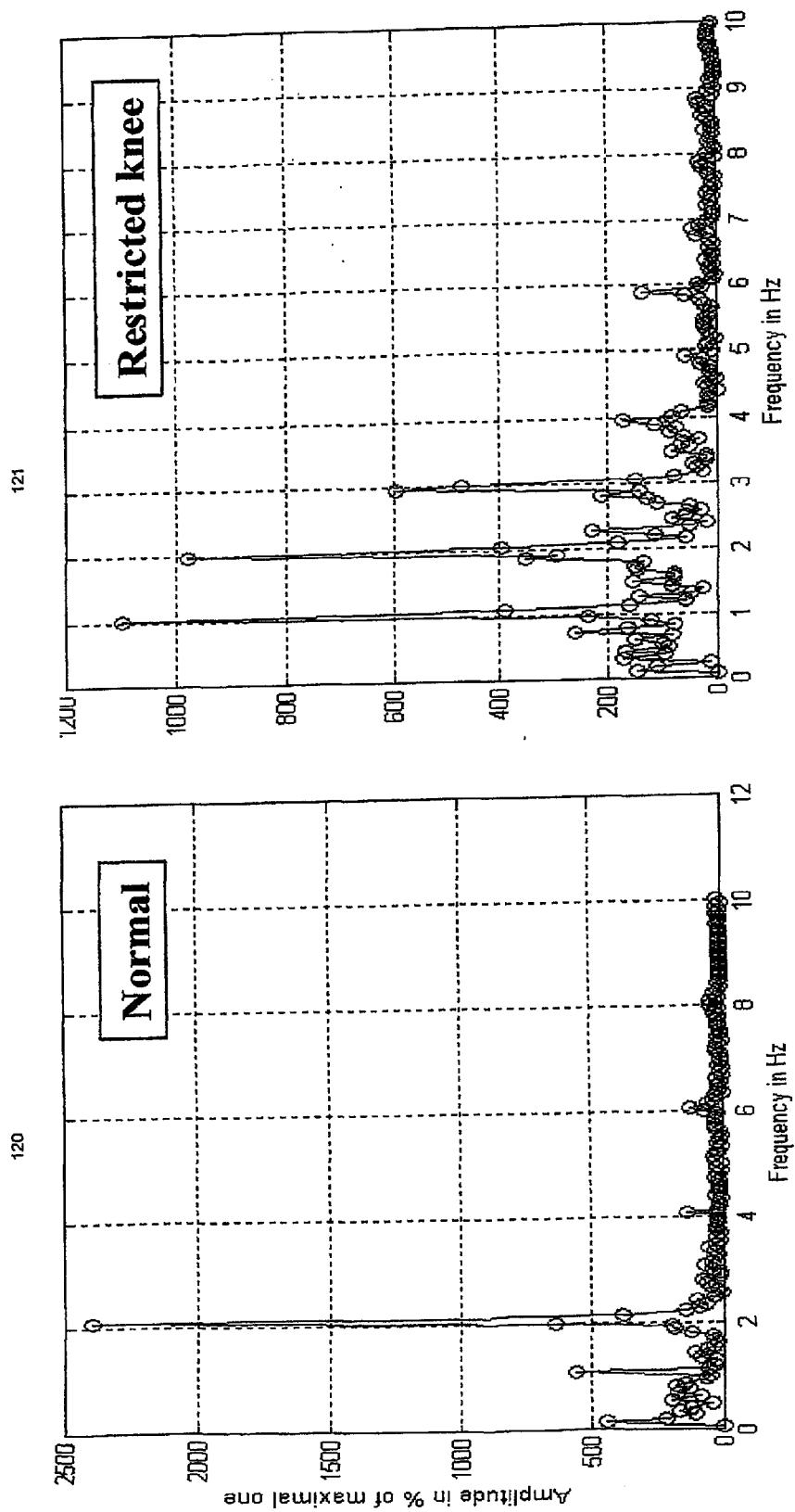
FIG. 12 is an exemplary graphical representation of the spectral density of walking in a straight line.

The graphs in FIG. 11 illustrate the above process. This graph shows the sagittal projection of the head summit motion vertical component. The X axis of the graph is the time reference in frames (i.e. 1/30 second per frame). The Y axis is a distance in pixels. Vertical motion is projected with a resolution of 1 pixel or 0.5 cm. The motion in the frontal plane is projected with a resolution of 1.5 cm. Markers in the graph show the various timing events on the curves. An asterisk marks the initial contact (IC), a square marks the initial push off (PO) and a circle marks the middle single support (MSS). RF is used to indicate the right step and LF is used to indicate the left step. The terminology of these events are common in the gait and balance laboratory. The left graph is a pattern of normal walking of a young man. The right graph in FIG. 11 corresponds to walking of the same man but with his right knee mechanically restricted. Frontal motion of the summit causes asymmetry in the height of the peaks. Nearer to the camera side produces higher peaks. This difference expressed in centimeters is rather close to the width of the walking base. The difference between the minimums is much smaller because the lowest points of the summit is very close to the central (sagittal plane) The knee stiffness produces asymmetry in the minimum deepness. Finally, fourier transforms of all of the above motion characteristics, including discrete sine- and cosine-transforms, power spectrum, etc. transforms may be calculated, see FIG. 12.

These motion characteristics, while not exhaustive of all motion characteristics that may be calculated based on motion portraits, may be used by a physician or other skilled practitioner to determine the existence of trends demonstrating improvement, deterioration or no change in a subject/patient's condition.

Alternatively, a comparison subsystem is provided. In particular, previous data including, but not limited to, motion portraits and/or motion characteristics data from one or more previous sessions with a given subject/patient, is stored. The previous data may also comprise normal data for the subject/patient, i.e., data corresponding to a time when the subject/patient was generally in good health. By comparing current motion characteristics and/or motion portraits with previous or normal motion characteristics/motion portraits, practitioners can detect difference between the two and, based on their experience and expertise, draw diagnostic conclusions.

As another alternative, motion characteristics data may be compared against predetermined thresholds (for example, determined based on an averaging of values for a given characteristic in a large sample of similarly situated subject/patients) to assess the subject/patient's condition. Health care practitioners and those generally having skill in the art will recognize that a variety of comparison and/or other analysis methods may be used in assessing a subject/patient's condition.

E. System of Motor Tasks and Protocol

The use of video image processing, as described, may be combined with a task oriented examination and diagnostic protocol. An example of such a protocol is discussed hereinafter. Briefly, a series of patient tests or exercises are specified for performance by the subject. Physiological measurement, qualitative analysis of the responses, quantitative recording of vital signs, and video imaging are all recorded with a composite result being indicative of the health of the subject. The subject will be diagnosed with respect to illness or infirmity and with healthy subjects, a normal baseline will be established. Thus the following protocol is an example which may be varied or alternative protocols may be adopted.

In order to properly exploit the power of such monitoring, a system of motor tasks and a protocol for carrying them out should be defined such that the different environment in which they are performed, is taken into account. In particular, motion, gait and balance testing should take into account the following conditions: (a) as a rule, the nervous system of the subject/patient is disordered because of age and/or disease; (b) absolute safety, i.e. a zero probability of falling during testing is required because of the absence of assistance that could provide a guarantee against an accidental fall; (c) only remote oral and visual instructions, warnings and explanations are available for fall prevention; (d) no expensive gait analysis techniques can be effectively used; (e) testing procedures should performed quickly and easily; (f) only one Pan-Tilt-Zoom type video camera is used; and (g) the monitoring technique and comprehensive examination must reveal any kind of change in the medical condition of the subject/patient relating to his balancing ability.

Although the last requirement seems to be incompatible with the previous conditions, a compromise can be found: (a) for nervous disorders, motor tasks can be ranked within one test, checking a specific kind of activity and not trying to arrange the tests by difficulty of implementation; (b) a protocol of examination, including conditions of audio visual recording, can be strictly standardized for a given subject/patient; (c) monitoring can be organized to make time-comparisons of the measurements and observations; (d) safety can be provided by extracting from the complete functional tests (from "Get Up and Go", for example) only the necessary tasks, and combining them so that they may be done near a wall, a chair back, corner or other similar support.

1. Instrumentation

An audio-visual recording system and image processing, as described above relative to FIGS. 1–4, is the preferred means for obtaining kinematic information resulting from performance of various tasks selected for a given subject/patient. As noted above, only one video camera is required for this purpose; it's orientation, zoom, shutter, gain and white balance can be controlled remotely from the central station. Optionally, other instruments may also be used, including an ECG instrument for indirect measurement of exertion or equipment to monitor quantitatively, e.g., blood pressure non-invasively before and after an exercise. Further still, additional video cameras may be used to monitor activities of the subject/patient or for comparative analyses and data acquisition from distinct orientations.

2. Tests and Tasks

In a preferred embodiment there are eleven (11) tests or groups of tasks. The tests are designed to enable checking all mechanical and nervous mechanisms of stability, and an exemplary set are listed in Appendix A with a more detailed explanation of each test set forth in Appendix B.

The procedure of the examination is adapted to conditions of monitoring in the home without any physical assistance though it may be used in a hospital or personally monitored environment. Safety is ensured through the use of verbal instructions and warnings. To further ensure safety, many tasks have been modified or even discarded, e.g., stepping over an obstacle, transferring, etc. Other tasks standard tasks have been modified to provide acceptable conditions for audio-visual recording in restricted room sizes, e.g., free level walking, changing speed, abrupt stop etc. All tasks including dynamic perturbations of balancing in standing are self-initiated without any use of external forces. As shown in Appendix A, each task is grouped under a corresponding test according to the test identification number. Furthermore, within each group of related tasks, the tasks are generally ranked in order of increasing difficulty.

3. Protocol of Examination

For any given subject/patient, about 8–10 tasks in total are selected from among the various tests as a basic check for regular monitoring. The basic check is performed to provide an entire body of physical and neurological information relating to balancing ability of the given subject/patient. Given the relatively small number of tasks to be completed, it is anticipated that the basic check or protocol can be performed in 5 to 7 minutes.

Ordering the tasks by their level of difficulty saves on the amount of tasks that have to be carried out because, for each test, it is generally enough to carry out only one or two tasks given the historical data for the subject/patient. That is, once a subject/patient has demonstrated an ability or inability to a test at a given level of difficulty, later examinations can be tailored to include only those tasks at the next higher or lower difficulties levels. Also, such a procedure is the most informative in that the maximum amount of the features are revealed. The practitioner immediately obtains the key value: the difficulty level that, together with relevant information from the conversation with the subject/patient, serves as a basis for continuing, interrupting or changing the current examination program. Of course, the tasks may be flexibly altered during an examination as deemed necessary by the practitioner. For example, where undesired changes are detected or ambiguous results obtained, the practitioner can investigate more thoroughly by asking the subject/patient to perform other tasks within the same test. In this manner, a definition may be arrived at according to either the predefined basic test scheme or a current decision of the practitioner.

As a result of task implementation, three kinds of data are provided: quantitative, qualitative and images. Quantitative data, such as temporal and spatial parameters of a gait cycle (i.e., the motion characteristics described above), resulting from analysis of image data are instrumental, being obviously objective assessments of a subject/patient's state. Appendix C lists quantitative variables that may be measured, the types of units (if any) applicable to each variable, and a data type used to express the value of each variable.

Qualitative data comes from observation (evoked balance strategies, anticipation reactions etc.) and special efforts are required for making this criteria fully objective. Appendix D first sets forth a list of Graded Results expressive of various qualitative variables. The Graded Scales list, also set forth in Appendix D, shows the various ranges or scales of measurements relative to each qualitative variable. In this manner, observations by practitioner may be translated into relatively objective data that may be tracked in a manner similar to the quantitative data.

Additionally, because all tasks within one test are arranged by their degree of difficulty, the order of the tasks becomes a benchmark value because of its objective nature. Stated another way, the difficulty level of each task inherently serves as a benchmark. In order to provide a fine scale for grading, a set of tasks, each with a minor increase in difficulty, is defined for benchmark testing. If the gap in such a "scale" becomes too large then a new task can be inserted. For example, a non-standard task "Standing on foot and opposite toe" covers the space between the "Two feet together" and the "One leg stance" tasks. Some of the tasks can be adjusted to a finer gradation with the help of certain mechanical parameters. For example, putting a weight on a subject/patient's wrist during the task "Dynamic Center of Gravity (COG) Shift" varies the difficulty level and could play the role of a fine calibration tool. Navigation of the subject/patient over such a set of benchmark data directly points to improvement or deterioration of his/her condition.

In summary, standard functional tests of gait and balance abilities in elderly subject/patients inadequately meet the requirements of the health monitoring service of ambulatory (in home) subject/patients as well as hospital site subject/patients. Therefore, the present invention proposes a technique, comprised of a specific approach to obtaining, analyzing and representing results; a set of tests mostly containing a subset of motor tasks; and a protocol of carrying out the examination. Results of the examination are divided into two parts: first, a level of difficulty of performance of a current motor task for a given subject/patient that immediately and objectively gives an initial approximation to a measurement of the motor ability of the subject/patient and, second, all other quantitative, graded qualitative results of measurements and image processing. Additionally, desired objective and fine monitoring are achieved by comparing session results with each other.

The set of tests is complete enough to check all essential aspects of the ability to maintain balance in rest, through steady locomotion and maneuvers. The tests are groups of motor tasks arranged by their level of difficulty. This arrangement may be quite individual for a given subject/patient with a certain combination of nervous and physiological disorders. The tasks are safe and informative. The protocol of examination provides validity through the comparison of session results. This is attained through the standardization (for each subject/patient) of the procedures of implementation and conditions of audio-visual recording. The protocol is adapted to home conditions and the absence of an assistant: for safety, all maneuvers are preferably carried out near the wall, corner or other support where necessary. Because a health care practitioner at the central station deals only with objective facts concerning the performance of the tasks, they are not burdened with the interpretation of results. A more skilled practitioner can then perform off-line analysis of the data obtained during the examination. One example of a task and their assessment correlating qualitative, quantitative, and video image results follows:

4. Example

Figure 13:
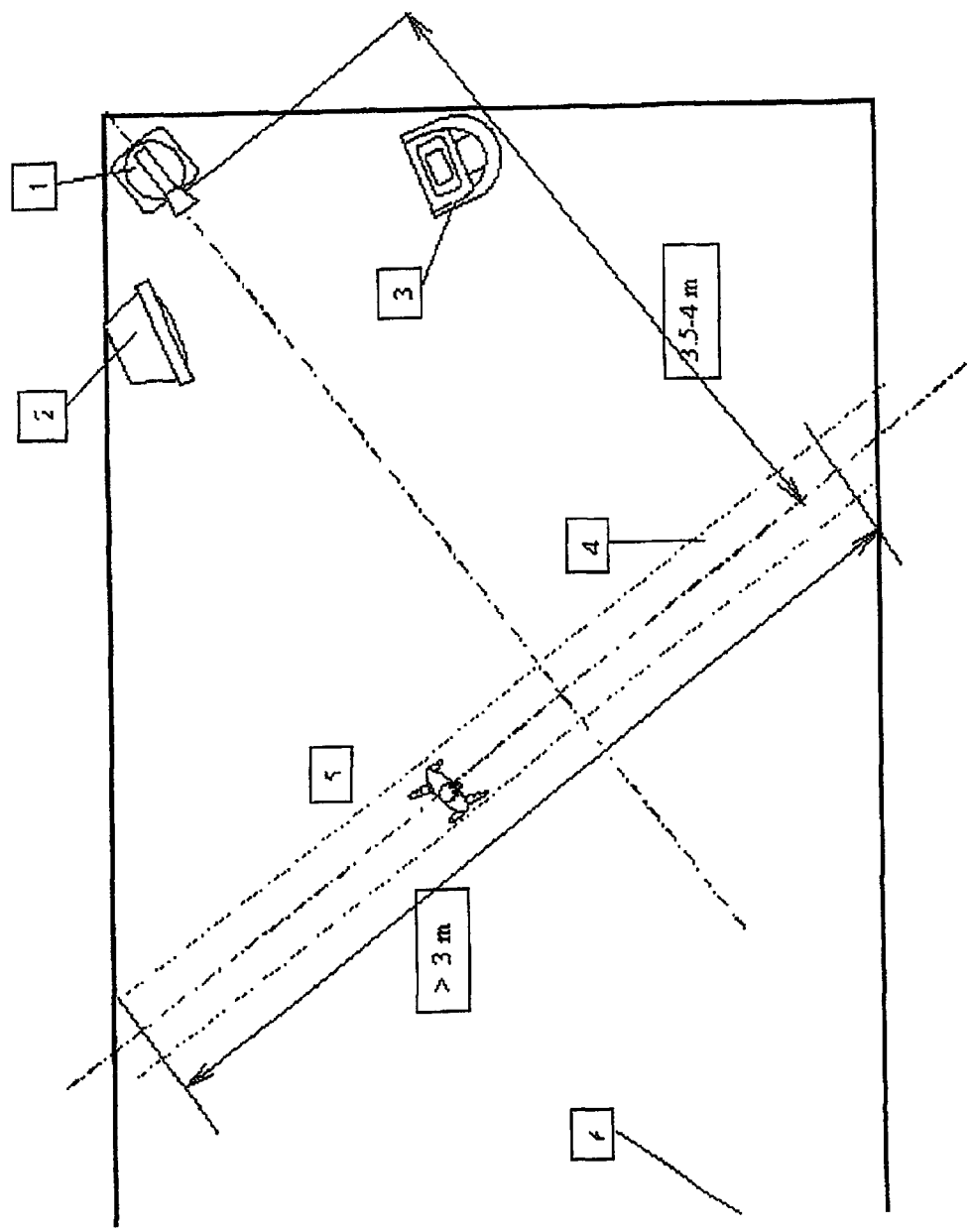
FIG. 13 is an exemplary home layout for walking in a straight line.
Figure 14:
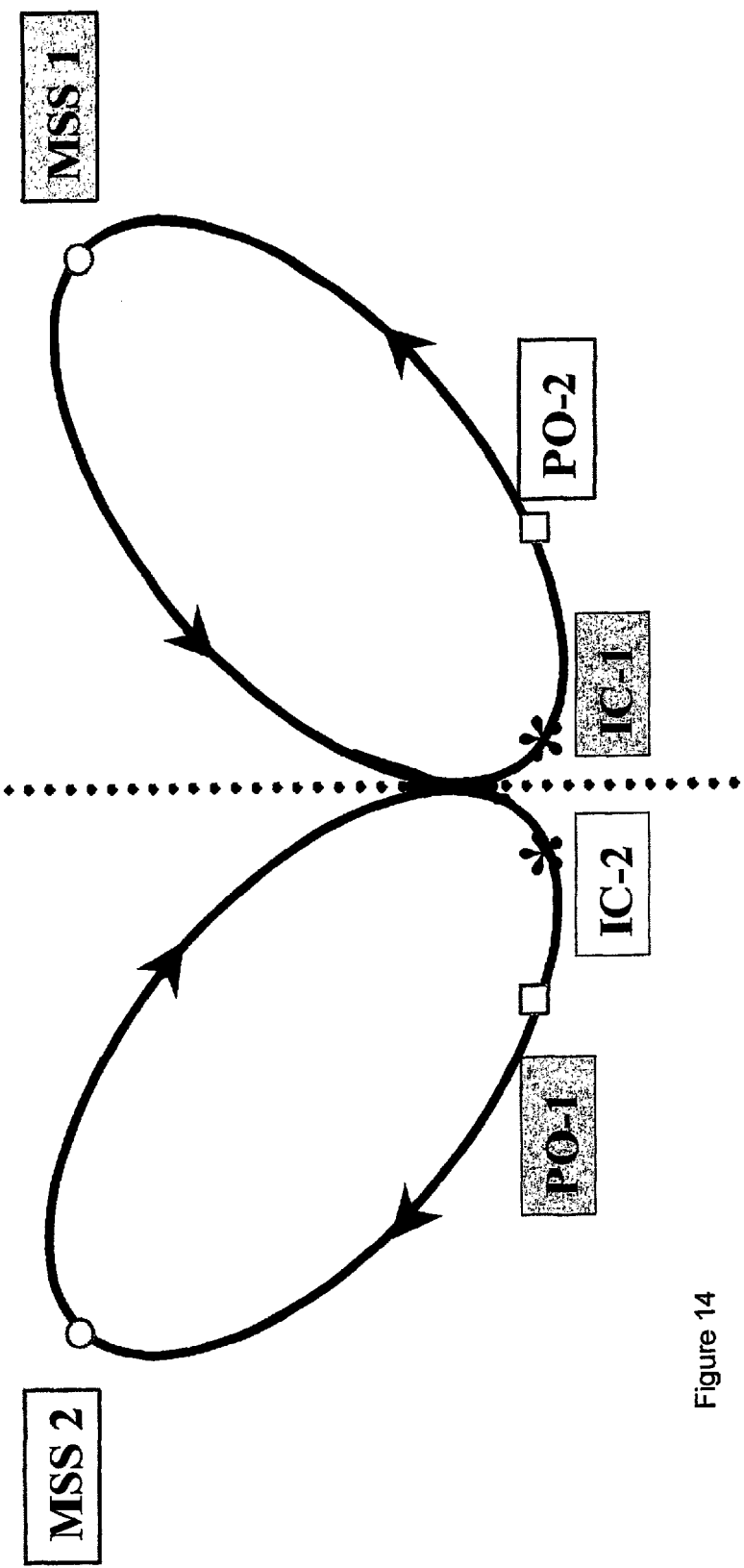
FIG. 14 is an exemplary drawing showing the sequence of events in a walking cycle.

One given test is produced by having the subject walk in a walk in a straight line perpendicular to the camera FIG. 13. The subject walks this path for a prescribed number of times. Each time the opposite side of the subject is close to the camera. The walk is filmed and transferred to the central station. The video images for each path are appended one to the other to obtain a longer time (i.e. more walking cycles) for statistical analysis. The image then goes through the preprocessing cycle to produce x and y segmentation matrices. Information pertaining to the gait and balance cycle for mid single support, push off, initial contact, see FIG. 14, are extracted for each cycle. The information is used to produce a graph such as shown in FIG. 11. The graph is then analyzed to build a table of data as shown in FIG. 15. The data in FIG. 15 along with the segmentation matrices are stored in the database. Abnormal data causes an alarm message to appear on the screen.

While the foregoing detailed description sets forth preferably preferred embodiments of the invention, it will be understood that many variations may be made to the embodiments disclosed herein without departing from the true spirit and scope of the invention. This true spirit and scope of the present invention is defined by the appended claims, to be interpreted in light of the foregoing specifications.

WO 01/88836                                                            PCT/US01/16180

APPENDIX A

TESTS

| ID | Name | Description |
|---|---|---|
| 10 | Conversation | Face, eyes, nose, O-ring, tremor etc. |
| 11 | Range of Motion (ROM) and strength | Musculoskeletal condition |
| 12 | Balancing in rest | Balancing in sitting and standing |
| 13 | Reach | Sitting and standing reach tests |
| 14 | Mechanical self-perturbation fast | Shift of the Center of Gravity caused by motions |
| 15 | Non mechanical self perturbation | Instability caused by slow head motion |
| 16 | Free walking | Level walking and walking in place |
| 17 | Complicated walking | Walking a line, tandem walking and etc. |
| 18 | Maneuvers | Stepping around an obstacle and so on |
| 19 | Single motor task | Sitting to standing and vise versa, etc. |
| 20 | Two motor tasks together | Gazing while walking, etc. |

TASKS

| ID | Name | Test ID | Difficulty level |
|---|---|---|---|
| 1001 | Gazing into the camera | 10 | Null |
| 1002 | O-ring fingers touching | 10 | Null |
| 1003 | Pupils light reaction | 10 | Null |
| 1004 | Nose test | 10 | Null |
| 1005 | Finger to finger test | 10 | Null |
| 1006 | Tremor while sitting | 10 | Null |
| 1007 | Writing | 10 | Null |
| 1101 | Dorsi-Plantar flexion in ankle | 11 | Null |
| 1102 | Pronation-supination in subtalar join | 11 | Null |
| 1103 | Knee flexion-Extension | 11 | Null |
| 1104 | Hip Flexion-Extension | 11 | Null |
| 1105 | Hip Adduction-Abduction | 11 | Null |
| 1106 | Hip Rotation | 11 | Null |
| 1107 | Gluteus medius strength | 11 | Null |
| 1108 | Frontal bending of the trunk | 11 | Null |
| 1109 | Twisting of the trunk | 11 | Null |
| 1110 | Neck mobility | 11 | Null |
| 1201 | Sitting, feet on the floor | 12 | 0 |
| 1202 | Sitting, feet unsupported | 12 | 1 |
| 1203 | Standing with a cane in front | 12 | 2 |
| 1204 | Bipedal standing with a pelvic size base | 12 | 3 |
| 1205 | Standing with both feet together | 12 | 4 |
| 1206 | Standing on the foot and tip-toe | 12 | 5 |
| 1207 | Standing on two tip-toes | 12 | 6 |
| 1208 | Standing on the tip-toe and a cane alongside | 12 | 7 |
| 1209 | Tandem standing | 12 | 8 |
| 1210 | Standing on one foot | 12 | 9 |
| 1211 | Standing on one tip-toe | 12 | 10 |

| 1301 | Sitting reach, anterior | 13 | 0 |
| 1302 | Sitting reach, lateral | 13 | 1 |
| 1303 | Standing reach, anterior | 13 | 2 |
| 1304 | Standing reach, lateral | 13 | 3 |
| 1401 | Self initiated sway | 14 | 0 |
| 1402 | COG shift caused by arm abduction | 14 | 1 |
| 1403 | COG shift caused by arm adduction | 14 | 1 |
| 1404 | Moving a gripped weight laterally | 14 | 2 |
| 1405 | Moving a gripped weight medially | 14 | 2 |
| 1406 | COG shift by leg abduction | 14 | 3 |
| 1407 | COG shift by leg adduction | 14 | 3 |
| 1501 | Balancing with head stretching up | 15 | 0 |
| 1502 | Balancing with head turning back & bowing | 15 | 1 |
| 1503 | Balancing with head turning | 15 | 2 |
| 1601 | Free level walking | 16 | 0 |
| 1602 | Free walking in place | 16 | 1 |
| 1701 | Free walking in place with eyes closed | 17 | 0 |
| 1702 | Free level walking with eyes closed | 17 | 1 |
| 1703 | Walking a line with normal step length | 17 | 2 |
| 1704 | 1703 + arms folded | 17 | 3 |
| 1705 | Tandem walking | 17 | 4 |
| 1801 | Ignition of walking | 18 | 0 |
| 1802 | Changing speed | 18 | 1 |
| 1803 | Abrupt stop | 18 | 2 |
| 1804 | Stepping around an obstacle | 18 | 3 |
| 1805 | Stepping on drawn or appearing targets | 18 | 4 |
| 1901 | Romberg with arms stretched forward | 19 | 0 |
| 1902 | Looking behind with trunk twisting | 19 | 1 |
| 1903 | Lateral walking | 19 | 2 |
| 1904 | Lateral walking with "scissors" | 19 | 3 |
| 1905 | Sitting to standing and vice versa | 19 | 4 |
| 1906 | Turn 180 degrees | 19 | 5 |
| 2001 | Shaking an imaginary hand with standing up | 20 | 0 |
| 2002 | Gazing into the camera while walking | 20 | 1 |

WO 01/88836                                                                  PCT/US01/16180

APPENDIX B

Tests And Tasks, Options, Protocol Descriptions, Durations And List Of Results 5   TEST 10: CONVERSATION
    Several motor tasks can be implemented during Conversation when patient's face, hands and
    feet are seen in details and patient is in a rest position in the armchair.
    <u>Task 1001: Gazing into the camera</u>
    *Description:*
10  An ability to gaze at a selected object despite of a relatively fast motion of the head
    hampering the gaze conditions.
    *Options:*
        1. Turning the head right and left; 2. Raising and bowing the head.
    *Protocol:*
15      <u>Initial mise-en-scene:</u> The patient sits in the armchair opposite to the camera leaning
        backward with hands on the arm-rests.
        <u>Camera settings:</u> front view, zoom in on the face and neck.
        <u>Instruction:</u> Sit quiet. Look at the camera for 3 sec. Try to gaze into the camera while
        turning your head right and left fast as possible but without any discomfort. Do 3
20      (three) cycles.
        [The same with raising and bowing the head]
    *Duration:*
        10 * 2 = 20 sec
    *Data registered by the operator:*
25      Task name, options applied, options fulfilled and failure causes.
    *Results, obtained by the analyzer:*
        Gazing quality (graded),
        Gazing features (composite), 30  <u>Task 1002: O-ring fingers touching</u>
    *Description:*
        Consequent touching of the thumb-tip by tip of all other fingers: index, middle,
        ring and little. The touching should be done as fast as possible and with eyes closed.
    *Options:*
35      1. Right hand, 2. Left hand.
    *Protocol:*
        <u>Initial mise-en-scene:</u>
            The patient sits in the armchair leaning to its back with hands on the arm-rests. He/
            she rises one hand a little, approximately to a chest level and turn it so that all
40          touches could be recognized by the camera.
        <u>Camera's settings:</u>
            Filming en face, zoom in on the working hand and the face.
        <u>Instruction:</u>
            Put your right hand into camera field of view so that your fingers motion will be seen
45          well. Ok! Make a cycle of touches to the thumb-tip by tips of all other fingers: the
            index, middle, ring, little, little, ring, middle and index fingers. Do the exercise 3
            (three) times.
            {The same for the left hand]
    *Duration:*

10 * 2 =20 sec
*Data registered by the operator:*
  Task name, options applied, options fulfilled and failure causes.
*Results obtained by the analyzer:*
  O-ring touches quickness (one value),
  O-ring touches hits (one value),
  Performance quality (graded)
  Face asymmetry (graded),
  Bags under the eyes (graded).

Task 1003: Pupils reaction to light
*Description:*
  Checks an acuteness of the pupils reaction to an abrupt change in illumination.
*Options:*
  None.
*Protocol:*
  Initial mise-en-scene:
    The patient sits straight in the armchair with hands on the arm-rests looking directly at the camera.
  Camera's settings:
    Filming en face, zoom in on the face.
  Instruction:
    Sit straight looking at the camera lens. Attention! Now the light will be increased for 3 - 5 sec. Try do not wink!
    [Repeat the task twice]
*Duration:*
  # 15 sec
*Data registered by the operator:*
  Task name, fulfillment and failure causes.
*Results obtained by the analyzer:*
  Pupils reaction (graded),
  Face asymmetry (graded),
  Bags under the eyes (graded).

Task 1004: Nose test
*Description:*
  Checks an ability to find with the eyes closed a tip of the nose with tip of the index-finger.
*Options:*
  1. By the right hand, 2. By the left hand.
*Protocol:*
  Initial mise-en-scene:
    The patient sits straight in the armchair with hands on the arm-rests looking directly at the camera.
  Camera's settings:
    Filming en face, zoom in on the face so that stretched outside arms could be placed inside the frame.
  Instruction:
    Close the eyes. Stretch your right arm outside with the index-finger extended. Touch your nose with tip of the index-finger. Put the hand in place. Do this exercise 3 (three) times. Open your eyes.
[Repeat the task for the left hand]
*Duration*:
15 * 2 = 30 sec
*Data registered by the operator:*
Task name, options applied, options fulfilled and failure causes.
*Results obtained by the analyzer:*
Successful attempts (one value),
Performance quality (graded),
Face asymmetry (graded),
Bags under the eyes (graded).

Task 1005: Finger to finger test
*Description*:
Checks an ability to match tips of the index-fingers while the eyes are closed.
*Options*:
1. Right to left, 2. Left to right.
*Protocol*:
Initial mise-en-scene:
The patient sits in the armchair opposite to the camera. The arms are bent in elbows and lifted a little so that hands are on the chest level and forearms are horizontal. The index-fingers match one another.
Camera's settings:
Filming en face, zoom in on the chest so that stretched outside arms were inside the frame.
Instruction:
Do several circular motions by your right hand and stretch your right arm outside. Then find the tip of your left (immovable) index-finger by the tip of your right index-finger. Ok!
Close your eyes and do this exercise 3 (three) times.
[Repeat the exercises for the left to right option]
*Duration*:
15 * 2 = 30 sec
*Data registered by the operator:*
Task name, options applied, options fulfilled and failure causes.
*Results obtained by the analyzer:*
Successful attempts (one value),
Performance quality (graded),
Face asymmetry (graded),
Bags under the eyes (graded).

Task 1006: Tremor while sitting
*Description*:
Checks an existence of a hands and/or feet tremor.
*Options*:
None.
*Protocol*:
Initial mise-en-scene:

The patient sits quietly in the armchair with the feet on the floor and hands on the knees. Whole sole's area contacts the floor.
Camera's settings:
Filming from the front, zoom in on the lower part of body so that feet and hands were inside the frame.
Instruction:
Sit quietly for 15 sec.
*Duration*:
15 sec
*Data registered by the operator:*
Task name.
*Results obtained by the analyzer:*
Tremor amplitude (one value),
Tremor frequency (one value),
Side and limbs involved (composite).

Task 1007: Writing
*Description*:
Check changes in handwriting that could be associated with the nervous disorders.
*Options*:
1. Right hand, 2. Left hand.
*Protocol*:
Initial mise-en-scene:
The patient sits at table or in the armchair with a clipboard on the knees and write or draw a certain text or a figure. Then he/she shows it to the camera.
Camera's settings:
Zoom in on the clipboard which is perpendicular to camera axis as strictly as possible.
Instruction:
Write (draw) your usual text (pattern) by right and left hands.
Please, show it to the camera.
*Duration*:
30 sec
*Data registered by the operator:*
Task name, options applied, options fulfilled and failure causes.
*Results obtained by the analyzer:*
Changes in handwriting,
Tremor of line drawing TEST 11: ROM AND STRENGTH
This set of motor tasks check a range of motion (ROM) in large joints and strength of main muscle groups associated with a gait and balance performance.
Task 1101 + 1103 + 1104: Dorsi-plantar flexion in ankle, knee and hip flexion-extension
*Description*:
Slow lifting and descending on the tip-toes permits to estimate an ability of the ankle. Lifting the thigh and bending in knee check hip and knee flexion. Knee and hip extension also are checking in this position.
Dorsiflexion under loading is tested in another position applying the weight of upper body to resist the dorsiflexion.

*Options*:
1. Right, 2. Left, 3. Dorsi with loading, Right, 4. Dorsi with loading, Left.
*Protocol*:
Initial mise-en-scene:
    Option 1:
The patient stands on the "walkway" with right side to the camera so that the
    sagittal plane is perpendicular to the camera axis. His/her left foot is lifted a little
    and left hand touches the wall or other support (a chair, quad-cane etc.).
    Option 3:
    The patient stands on the "walkway" right side to the camera. He/she presses by
    long enough T-shape rod (quad-cane, swab, wiper etc.) on to right toe with all his/
    her weight (or part of it) in order to load the forefoot.
Camera's settings:
    Filming from side.
    Options 1 and 2: two feet and hand holding a support must be in the frame. Space
        between the floor and heel must be easy recognized.
    Options 3 and 4: Loaded foot and rod must be in the frame. Space between the
        toe and the floor must be easy recognized.
Instruction:
    Task 1101. Options 1 and 2: Lift yourself on tip-toe slowly, keep so for 3 sec and
        lower as slowly as possible. Repeat the exercise twice.
    Tasks 1103 &1104. Option 1: Bend your right knee as much as possible with slight
        bending of the hip. Keep it so for 1 - 2 sec. Lift the thigh as high as possible with
        knee bent. Keep it so for a second and try to straight the leg (extend the knee).
        Put the heel on the floor in front of you a little and try to extend it up to end, it is
        possible to press slightly the knee by the right hand. Stand straight.
        Raise your right heel as it possible by flexing the knee with thigh vertical. Try to
        extend the hip (move it backward) without leaning the trunk forward. Try to extend
        the knee and keep so for a second.
    Turn 180☐ , stay straight and do the same with the left side.
    Options 3 and 4: Press the rod strongly with help of your trunk weight. Try to lift the
        toe. If that is impossible decrease the load by straightening out gradually. Fit the
        appropriate load and try to lift the toe. Repeat the exercise twice.
*Duration*:
    Options 1 & 2: 15 * 4 = 60 sec.
    Options 3 & 4: 5 * 4 = 20 sec.
*Data registered by the operator:*
    Task name, options applied, options fulfilled and failure causes.
*Results obtained by the analyzer:*
    Slow lifting time (one value),
    Slow descending time (one value),
    Foot to floor angle (one value),
    Range of motion grade (graded),
    Loading grade (graded),
    Knee flexion (one value),
    Knee extension (one value),
    Hip flexion (one value),
    Hip extension (one value).

WO 01/88836  PCT/US01/16180

Tasks 1102 +1106+1107
   *Description:*
      Task 1102 checks a mobility in subtalar joints, 1006 checks rotation in hip joints and
      1107 checks ability of gluteus medius to lift the pelvic hemisphere with attached leg.
      The all three tasks need the same initial pose therefore it is reasonable to carry out
      them together.
   *Options:*
      1. Right, 2. Left.
   *Protocol:*
   Initial mise-en-scene:
      The patient stand with his back to wall 15 - 20 cm apart. He/she is supported by the
      elbows touching the wall and the forearms are near to be perpendicular to the wall.
   Camera's settings:
      Filming from front. The camera axis is perpendicular to the frontal plane. The whole
      body is in the frame. When pelvic hemisphere is lifted the space under foot,
      supination and pronation of the foot must be seen evidently.
   Instruction:
      Stand straight. You have to raise the pelvic hemispheres by turns without help of
      your trunk bending.
      Raise as high as it is possible your right pelvic hemisphere with the leg hung as a
      log (stretched down). Keep it so for three seconds.{Task 1107}. Rotate your right
      leg in the hip out and inside 3 (three) times {Task 1106} and then supinate and
      pronate the foot also 3 (three) times {Task 1102}.
      [Repeat the same exercise for left side].
   Notation: if the gluteus medius is too weak to lift the leg remarkably do that with
      help of trunk bending to check at least mobility in the hip and subtalar joints.
   *Duration:*
      15 * 2 = 30 sec
   *Data registered by the operator:*
      Tasks name, options applied, options fulfilled and failure causes.
   *Results obtained by the analyzer:*
      Task 1102: Foot pronation (graded),
              Foot supination (graded).
      Task 1106: Hip rotation, external (graded),
              Hip rotation, internal (graded).
      Task 1107: Pelvic obliquity (one value).

Task 1105: Hip Abduction-adduction
   *Description:*
      Checks the lateral and medial movement of the legs.
   *Options:*
      1. Right, 2. Left.
   *Protocol:*
   Initial mise-en-scene:
      The patient stands back to the camera and face to a wall or any other support.
      He/she puts the both hand on the support on the chest or shoulders level.
   Camera's settings:
      Filming from back. The camera axis is perpendicular to a coronal plane. Tee whole
      body is in the frame.

32

Instruction:
Raise your right leg outside as high as possible. Keep it there for 1-2 seconds.
Move it inside (behind the left leg) as far as possible. Keep it so for 1-2 seconds.
Do this exercise twice.
[Repeat the task for the left leg].
*Duration*:
10 * 2 = 20 sec
*Data registered by the operator:*
Task name, options applied, options fulfilled and failure causes.
*Results obtained by the analyzer:*
Hip abduction (one value),
Hip adduction (one value).

Task 1108: Frontal bending of the trunk
*Description*:
ROM of a frontal inclination of the trunk
*Options*:
1. Right side, 2. Left side.
*Protocol*:
Initial mise-en-scene:
The patient stands straight on the "walkway" face to the camera with arms hanging free and feet with the shoulder size distance.
Camera's settings:
Filming from the front, the camera axis is perpendicular to the coronal plane. Whole body is in the frame.
Instruction:
Bend rather slowly your trunk to the right side as far as possible without twisting it.
Slowly return to the straight pose. Do this exercise to the left side.
Do this cycle twice.
*Duration*:
10 * 2 = 20 sec
*Data registered by the operator:*
Task name, options applied, options fulfilled and failure causes.
*Results obtained by the analyzer:*
Trunk bending (graded).

Task 1109: Trunk twisting
*Description*:
Checks the ROM of trunk twisting, e.g. mutual rotation of the pelvis and shoulder girdle.
*Options*:
1. Clockwise, 2. Counter-clockwise.
*Protocol*:
Initial mise-en-scene:
The patient stands opposite to the camera on the "walkway" with his/her right side 'looking" at the camera. The arms are hanged free.
Camera's settings:
Filming from side. The camera axis is perpendicular to the sagittal plane of the body. The whole body is in the frame.

Instruction:
   Move your right shoulder forward and right pelvic hemisphere backward rather slowly as far as possible. Keep so for a second. Return to the initial posture. Now move the right shoulder backward and the pelvic hemisphere forward. Return.
   [Do the exercise twice].
Duration:
   10 * 2 = 20 sec.
Data registered by the operator:
   Task name, options applied, options fulfilled and failure causes.
Results obtained by the analyzer:
   Trunk twisting (graded)

Task 1110: Neck mobility
Description:
   The task checks ROM of the neck movements at straight standing.
Options:
   1.Clockwise, 2.Counter-clockwise, 3. Up, 4.Down, 5. Right, 6.Left
Protocol:
   Initial mise-en-scene:
      The patient stands on the 'walkway" face to the camera with arms hanging free.
   Camera's settings:
      Filming from the front. The camera axis is perpendicular to the coronal plane. Zoom in on the face and neck. The chest, neck and head are in the frame.
   Instruction:
      Turn your head slowly clockwise and counter-clockwise. look at the camera for a second after returning to the initial pose.
      Raise and bow your head slowly with maximal range. Look at the camera for a second when you are in the initial pose.
      Bend your neck rightward and leftward rather gently. Look at the camera after the return.
      Do this exercise twice.
   Duration:
      15 * 2 = 30 sec.
   Data registered by the operator:
      Task name, options applied, options fulfilled and failure causes.
   Results obtained by the analyzer:
      Neck twisting (graded),
      Neck bending (graded).

TEST 12: BALANCING IN REST
   This test defines the ability to keep balance in the most complex poses for the given patient. Thus, most balancing mechanisms manifest themselves.
Task 1201: Sitting with the feet supported
   Description:
      Easiest test on balancing. Only rescue and preventing reactions could be evoked.
   Options:
      1.Eyes opened, 2. Eyes closed.
   Protocol:
      Initial mise-en-scene:

WO 01/88836 PCT/US01/16180

The patient sits in front of the camera in the armchair with a horizontal seat
and relatively straight back. The feet are supported (reach the floor with whole area).
The arms are on the knees or folded. The patient does not lean the chair-back or
arm-rests.
If stool is used the patient sits in a corner or in the place that prevents from falls
backward and to sides when the balance will be lost.
Camera's settings:
Filming from the front. Whole body is in the frame.
Instruction:
{Close your eyes}. Try to sit straight as possible for 1 min. {Open your eyes in the
minute or if the balance will be lost}.
*Duration:*
60 sec or less.
*Data registered by the operator:*
Task name, options applied, options fulfilled and failure causes.
*Results obtained by the analyzer:*
Balancing time (one value),
Evoked balancing strategies (composite).

Task 1202: Sitting, the feet are unsupported
*Description:*
Check the balancing ability in less stable situation then in task 1201.
*Options:*
1. Eyes are opened, 2. Eyes are closed.
*Protocol:*
Initial mise-en-scene:
The patient sits in front of the camera in the armchair with a horizontal seat
and relatively straight back. The feet are unsupported (are in the air).
The arms are on the knees or folded. The patient does not lean the chair-back or
arm-rests.
If stool is used the patient sits in a corner or in the place that prevents from falls
backward and to sides when the balance will be lost.
Camera's settings:
Filming from the front. The camera axis is perpendicular to the coronal plane. Whole
body is in the frame.
Instruction:
{Close your eyes}. Try to sit straight as possible for 30 sec. {Open your eyes in the
half a minute or if the balance will be lost}.
*Duration:*
30 sec or less.
*Data registered by the operator:*
Task name, options applied, options fulfilled and failure causes.
*Results obtained by the analyzer:*
Balancing time (one value),
Evoked balancing strategies (composite).

Task 1203: Standing with a cane in front
*Description:*
This "tripod" is easier for balancing than bipedal standing and more difficult than sitting.

35

The difficulty of the performance may be fitted by variation of a distance between the quad-cane and feet.
*Options*:
1. Eyes are opened, 2. Eyes are closed.
*Protocol*:
Initial mise-en-scene:
The patient stands on the "walkway" opposite to the camera slightly supporting on the cane located in front.
Camera's settings:
Filming from the front. The camera axis is perpendicular to the coronal plane. Whole body is in the frame.
Instruction:
{Close your eyes}. Try to stand straight as possible for 60 sec. {Open your eyes in the minute or if the balance will be lost}.
*Duration*:
60 sec or less.
*Data registered by the operator:*
Task name, options applied, options fulfilled and failure causes.
*Results obtained by the analyzer:*
Balancing time (one value),
Cane to feet distance (one value),
Evoked balancing strategies (composite).

Task 1204: Bipedal standing with a pelvic size base
*Description*:
Easiest standing position for balancing.
*Options*:
1. Eyes are opened, 2. Eyes are closed.
*Protocol*:
Initial mise-en-scene:
The patients stands on the "walkway", face to the camera with his/her legs parallel. Such distance between feet is the reference base. The arms are hanged free.
Camera's settings:
Filming from the front. The camera axis is perpendicular to the coronal plane. Whole body is in the frame.
Instruction:
{Close your eyes}. Try to stand straight as possible for one minute. {Open your eyes in the minute or when the balance will be lost}.
*Duration*:
60 sec or less.
*Data registered by the operator:*
Task name, options applied, options fulfilled and failure causes.
*Results obtained by the analyzer:*
Balancing time (one value),
Evoked balancing strategies (composite).

Task 1205: Standing with two feet together
*Description*:
Bipedal standing with a narrow base is more difficult than with a wide one.

*Options*:
1. Eyes are opened, 2. Eyes are closed.
*Protocol*:
Initial mise-en-scene:
  The patients stands on the "walkway", face to the camera with his/her legs close one to another. The arms are hanged free.
Camera's settings:
  Filming from the front. The camera axis is perpendicular to the coronal plane. Whole body is in the frame.
Instruction:
  {Close your eyes}. Try to stand straight as possible for half a minute. {Open your eyes in the half of a minute or when the balance will be lost}.
*Duration*:
  30 sec or less.
*Data registered by the operator:*
  Task name, options applied, options fulfilled and failure causes.
*Results obtained by the analyzer:*
  Balancing time (one value),
  Evoked balancing strategies (composite).

Task 1206: Standing on the foot and tip-toe
*Description*:
  Bipedal standing with a narrow base and decreased area is more difficult than previous task. The foot_tip-toe base is an adjusting parameter changing the difficulty of the task performance.
*Options*:
  1. Eyes are opened and the right tip-toe, 2.Eyes are opened and the left tip-toe,
  3. Eyes are closed and the right tip-toe, 4.Eyes are closed and the left tip-toe.
*Protocol*:
Initial mise-en-scene:
  The patients stands on the "walkway", face to the camera, on the feet and opposite tip-toe. The arms are hanged free.
Camera's settings:
  Filming from the front. The camera axis is perpendicular to the coronal plane. Whole body is in the frame.
Instruction:
  {Close your eyes}. Try to stand straight as possible for half a minute. {Open your eyes in the half of a minute or when the balance will be lost}.
*Duration*:
  30 sec or less.
*Data registered by the operator:*
  Task name, options applied, options fulfilled and failure causes.
*Results obtained by the analyzer:*
  Balancing time (one value),
  Foot_tip-toe base (one value),
  Evoked balancing strategies (composite).

Task 1207: Standing on the two tip-toes
*Description*:

Bipedal standing with a narrow base and decreased area is more difficult than previous task. The two tip-toes base is an adjusting parameter changing the difficulty of the task performance.
*Options*:
  1. Eyes are opened , 2.Eyes are closed .
*Protocol*:
  Initial mise-en-scene:
    The patients stands on the "walkway", face to the camera, on the two tip-toes. The arms are hanged free.
  Camera's settings:
    Filming from the front. The camera axis is perpendicular to the coronal plane. Whole body is in the frame.
  Instruction:
    {Close your eyes}. Try to stand straight as possible for 15 sec. {Open your eyes in 15 sec or when the balance will be lost}.
*Duration*:
  15 sec or less.
*Data registered by the operator:*
  Task name, options applied, options fulfilled and failure causes.
*Results obtained by the analyzer:*
  Balancing time (one value),
  Two tip-toes base (one value),
  Evoked balancing strategies (composite).

Task 1208: Standing on the tip-toe and a cane alongside
*Description*:
  Bipedal standing with a less supporting area than in previous task. The cane_tip-toe base is an adjusting parameter changing the difficulty of the task performance.
*Options*:
  1. Eyes are opened and the right tip-toe, 2.Eyes are opened and the left tip-toe,
  3. Eyes are closed and the right tip-toe, 4.Eyes are closed and the left tip-toe.
*Protocol*:
  Initial mise-en-scene:
    The patients stands on the "walkway", face to the camera, on the tip-toe and a cane alongside . The opposite foot is lifted a little and the arm is hanged free. The hand located on the tip-toe side slightly holds the cane. The height of the cane is fitted so that the patient stands straight.
  Camera's settings:
    Filming from the front. The camera axis is perpendicular to the coronal plane. Whole body is in the frame.
  Instruction:
    {Close your eyes}. Try to stand straight as possible for 15 sec. {Open your eyes in 15 sec or when the balance will be lost}.
*Duration*:
  15 sec or less.
*Data registered by the operator:*
  Task name, options applied, options fulfilled and failure causes.
*Results obtained by the analyzer:*
  Balancing time (one value), Cane_tip-toe base (one value),
Evoked balancing strategies (composite).

Task 1209: Tandem standing
*Description*:
Bipedal standing with a narrow base when one foot is located just behind of the second one often is very difficult for balancing because the role of the feet strategy is reduced. If the stepping strategy is inadequate or absent then the task should be carrying out in a corner or in the place providing support on both sides.
*Options*:
1. Eyes are opened and right leg ahead, 2. Eyes are opened and left leg is ahead,
3. Eyes are closed and right leg ahead, 4. Eyes are closed and left leg is ahead,
*Protocol*:
Initial mise-en-scene:
The patients stands on the "walkway", face to the camera, in the tandem pose. The arms are hanged free. If there is not confidence in patient's stepping strategy of balancing he/she must to stand in a corner or in the other place providing an emergent support from sides.
Camera's settings:
Filming from the front. The camera axis is perpendicular to the coronal plane. Whole body is in the frame.
Instruction:
{Close your eyes}. Try to stand straight as possible for 15 sec. {Open your eyes in 15 sec or when the balance will be lost}.
*Duration*:
15 sec or less.
*Data registered by the operator:*
Task name, options applied, options fulfilled and failure causes.
*Results obtained by the analyzer:*
Balancing time (one value),
Evoked balancing strategies (composite).

Task 1210: Standing on the one foot
*Description*:
Standing on one foot is difficult because of asymmetry and decreased possibility to control the balance by means of a proprioceptive mechanism (so called, feet strategy).
*Options*:
1. Eyes are opened and the right leg, 2.Eyes are opened and the left leg,
3. Eyes are closed and the right leg, 4.Eyes are closed and the left leg.
*Protocol*:
Initial mise-en-scene:
The patients stands on the "walkway", face to the camera, on the one foot. The opposite foot is lifted a little and the arm is hanged free.
Camera's settings:
Filming from the front. The camera axis is perpendicular to the coronal plane. Whole body is in the frame.
Instruction:
{Close your eyes}. Try to stand straight as possible for 15 sec. {Open your eyes in 15 sec or when the balance will be lost}.

*Duration:*
   15 sec or less.
*Data registered by the operator:*
   Task name, options applied, options fulfilled and failure causes.
*Results obtained by the analyzer:*
   Balancing time (one value),
   Evoked balancing strategies (composite).

Task 1211: Standing on the one tip-toe
   *Description:*
      Standing on one tip-toe is most difficult task because of asymmetry and absence of
      the possibility to control the balance by means of a proprioceptive mechanism (so
      called, feet strategy).
   *Options:*
      1. Eyes are opened and the right tip-toe, 2.Eyes are opened and the left tip-toe,
      3. Eyes are closed and the right tip-toe, 4.Eyes are closed and the left tip-toe.
   *Protocol:*
      Initial mise-en-scene:
         The patients stands on the "walkway", face to the camera, on the one tip-toe. The
         opposite foot is lifted a little and the arm is hanged free.
      Camera's settings:
         Filming from the front. The camera axis is perpendicular to the coronal plane.
         Whole body is in the frame.
      Instruction:
         {Close your eyes}. Try to stand straight as possible for 10 sec. {Open your
         eyes in 10 sec or when the balance will be lost}.
   *Duration:*
      10 sec or less.
   *Data registered by the operator:*
      Task name, options applied, options fulfilled and failure causes.
   *Results obtained by the analyzer:*
      Balancing time (one value),
      Evoked balancing strategies (composite).

TEST 13: REACH
   The so-called reach tests (i.e., while the patient inclines as a piece of a log trying to
move his/her COG up to the physical or geometrical limits of stability) are good predictors of
the occurrence of falls. The reach tests are rather dangerous without any assistance and must be
carried out in a corner and/or near a wall to prevent fall during examination. Therefore,
generally, the camera axis and reach direction are not perpendicular each to other and an error
in definition of the reach distance is unpredictable. To avoid this inaccuracy the calibrated
cylinder is put on the arm stretched out in reach direction during the examination. The ratio
between reach distance and the cylinder is independent of angle of view and desired value can
be obtained in absolute units (cm, inches etc.).

Task 1301: Sitting reach, anterior
   *Description:*
      The patient sits on a stool or in an armchair with a horizontal seat and low arm-rests
      with the feet lifted a little. He/she stretches out both arms forward and tries to reach the wall in front of him/her until stepping on the floor. The distance corresponding to
a slow voluntary motion is measured.
*Options*:
*Protocol*:
Initial mise-en-scene:
The patient sits on a stool or in armchair before the wall (or an other barrier) with the
legs slightly lifted and arms stretched out forward and almost horizontally. The
distance to the wall is 5 - 10 cm longer then maximal reach distance for the given
patient. The patient is turned to the camera by side so that the mentioned above
cylinder can be seen by the camera. An angle of view must be right as possible but
deviation up to 30 degree are acceptable.
Camera's settings:
Filming from the side. The camera axis is perpendicular to the sagittal plane as
possible. Whole body is in the frame.
Instruction:
Reach the wall {barrier} slowly, try to keep yourself from abrupt achievement of the
wall {barrier}. Drop your feet on the floor and touch the wall when balancing will be
too hard.
*Duration*:
10 sec or less.
*Data registered by the operator:*
Task name, fulfillment and failure causes.
*Results obtained by the analyzer:*
Reach sagittal (one value).

Task 1302: Sitting reach, lateral
*Description*:
The patient sits on a stool or in an armchair with a horizontal seat and low arm-rests
with the feet lifted a little. He/she stretches out both arms outside and tries to reach
the wall in side of him/her until stepping on the floor. The distance corresponding to
a slow voluntary motion is measured.
*Options*:
1. Right, 2. Left.
*Protocol*:
Initial mise-en-scene:
The patient sits on a stool or in armchair in a corner or with a wall on the right side.
His/her legs are slightly lifted and arms stretched outside almost horizontally. The
distance to the walls is 5 - 10 cm longer then maximal reach distance for the given
patient. The patient is turned to the camera by the face (or the back) that the
mentioned above cylinders can be seen by the camera. An angle of view must be
right as possible but deviation up to 30 degree are acceptable.
Camera's settings:
Filming from the front (or the back). The camera axis is perpendicular to the sagittal
plane as possible. Whole body is in the frame.
Instruction:
Reach the wall slowly, try to keep yourself from abrupt achievement of the wall
Drop your feet on the floor and touch the wall when balancing will be too hard.
*Duration*:
10 * 2 = 20 sec or less.

*Data registered by the operator:*
    Task name, options applied, options fulfilled and failure causes.
*Results obtained by the analyzer:*
    Reach lateral (one value).

Task 1303: Standing reach, anterior
    *Description:*
        The patient stands before wall. He/she stretches out both arms forward and tries to
        reach the wall. The distance corresponding to a slow voluntary motion is measured.
    *Options:*
    *Protocol:*
        Initial mise-en-scene:
            The patient stands before the wall (or an other barrier) with arms stretched out
            forward and almost horizontally. The distance to the wall is 5 - 10 cm longer then
            maximal reach distance for the given patient. The patient is turned to the camera by
            side so that the mentioned above cylinder may be seen by the camera. An angle of
            view must be right as possible but deviation up to 30 degree are acceptable.
        Camera's settings:
            Filming from the side. The camera axis is perpendicular to the sagittal plane as
            possible. Whole body is in the frame.
        Instruction:
            Reach the wall {barrier} slowly, try to keep yourself from abrupt achievement of the
            wall {barrier}. Step forward and touch the wall when balancing will be too hard.
    *Duration:*
        10 sec or less.
    *Data registered by the operator:*
        Task name, fulfillment and failure causes.
    *Results obtained by the analyzer:*
        Reach sagittal (one value).

Task 1304: Standing reach, lateral
    *Description:*
        The patient stands in a corner, face to the walls, stretches both arms outside and tries
        to reach the walls in side of him/her until leaning the wall. Such pose provides
        safety on the stage of the balance loss. In contrary, reach while standing face to
        the camera is very dangerous. The distance corresponding to a slow voluntary motion
        is measured.
    *Options:*
        1. Right, 2. Left.
    *Protocol:*
        Initial mise-en-scene:
            The patient stands in a corner, back to the camera, the arms stretched outside
            almost horizontally. The distance to the walls is 5 - 10 cm longer then maximal reach
            distance for the given patient. The patient is turned to the camera by the back, the
            mentioned above cylinders can be seen by the camera. An angle of view must be
            right as possible but deviation up to 30 degree are acceptable.
        Camera's settings:
            Filming from the back. The camera axis is perpendicular to the sagittal plane as
            possible. Whole body is in the frame.

Instruction:
Reach the wall slowly, try to keep yourself from abrupt achievement of the wall
Step aside and touch the wall when balancing will be too hard.
*Duration*:
10 * 2 = 20 sec or less.
*Data registered by the operator:*
Task name, options applied, options fulfilled and failure causes.
*Results obtained by the analyzer:*
Reach lateral (one value).

TEST 14: MECHANICAL SELF-PERTURBATION
Resistance to mechanical perturbation may be assessed in home conditions only by self-perturbation methods when a fast shift of COG is created by means of relevant body movements. Although it is impossible to simulate the unexpected external disturbance such as a trip or collision in a crowded place but the self-induced disturbances occurring in everyday activity (bending, turning, transferring and so on) may be simulated. Moreover, only the self-induced shifts of COG reveal very important mechanism of anticipatory reactions to an arisen toppling force. Simulation of an external pushes requires a special equipment as a dynamic force plate and preventing falls assistance. Therefore it can not be realized under usual home conditions.

But with help of the self-initiated disturbances the all balancing strategies can be revealed and estimated. The good common sense combined with an adequate stepping strategy provide the good resistance to the external perturbations.

The task with the difficulty level preceded to the difficulty level of the hardest for a given patient task is selected for an examination with a self-initiated mechanical perturbation.

Task 1401: Self-initiated sway
*Description*:
The patient swings himself with increasing amplitude until he/she will be forced to make a step. The eyes are closed. For safety the patient stands with a distance from his back to a wall about 30 - 35 cm. The sagittal sway is measured relative to the foot length and the frontal sway is measured relative to a reference base (when the legs are parallel).
*Options*:
1. Sagittal, 2. Frontal
*Protocol*:
Initial mise-en-scene:
Option 1: The patient stands in a corner, back to the wall and side to the camera, the arms are hanged free. The leg are parallel. The feet are parallel to the sagittal plane as possible. If only one foot can to be parallel to the sagittal plane then this side is turned to the camera. The distance to the wall is 35 - 40 cm.
Option 2: The patient stands in the corner back to the camera and face to the corner.
His leg are parallel. The distance to the corner is about 70 cm. The upper arms
are close to sides of the trunk. The forearms are lifted with the palms "looking" forward. The pose is straight but without excessive tension. The palms provides support when the sway will exceed the limits of stability.
Camera's settings:
Option 1: Filming from the side. The camera axis is perpendicular to the sagittal plane as possible. Whole body is in the frame.

43

Option 2: Filming from the back. The camera axis is parallel to the sagittal plane as possible. Whole body is in the frame.

Instruction:
Option 1: Close your eyes. Swing yourself around the ankle forward and backward without bending in the hip and knee (as a piece of log). Increase gradually the range of your oscillation until you will lean the wall or make a step forward.
Option 2: Close your eyes. Swing yourself right and left around the feet without bending the trunk. Increase gradually the range of your oscillations until your palms will touch the walls.

Duration:
10 * 2 = 20 sec or less.

*Data registered by the operator:*
Task name, options applied, options fulfilled and failure causes.

*Results obtained by the analyzer:*
Sway anterior (one value),
Sway posterior (one value),
Sway frontal, right (one value),
Sway frontal, left (one value),
Balancing strategies (composite).

Tasks 1402 + 1403: COG shift caused by arm abduction and adduction

*Description*:
The perturbation is initiated by abduction and adduction (lifting and lowering) of the arm.
The possibility of stepping must be provided. If the patient stands on the one leg then a wall must be near to him on the supporting side and opposite arm is free for the movement. If the patient stands in bipedal pose then he/she must be in a corner back to the camera. The space between body and wall has to be about 40 - 50 cm.
It is possible to belt the forearm with soft gymnastic weight in order to enhance the perturbation. This weight is a parameter of monitoring.

*Options*:
1. Right, 2. Left, 3. Reference test.

*Protocol*:
Initial mise-en-scene:
The patient stands in a corner, side to the wall and face or back to the camera, the arms are hanged free. The distance to the wall is 35 - 40 cm.

Camera's settings:
Filming from the front or back. The camera axis is parallel to the coronal plane as possible. Whole body is in the frame.

Instruction:
Keep the balance for 3 sec and if you will feel yourself steady lift your right {left} arm outside as fast as possible and keep it horizontally. Try to keep the balance in the new position for 10 sec.
Stand in the initial position but with your right {left} arm stretched outside horizontally. Keep the balance for 3 sec and if you feel yourself steady lower your arm as fast as possible. Try to keep the balance for 10 sec.
Turn 180°
Repeat the exercise for the second arm.

*Duration*:

44

15 * 4 = 60 sec or less.
*Data registered by the operator:*
   Tasks name, options applied, options fulfilled and failure causes.
*Results obtained by the analyzer:*
   Perturbation time (one value),
   Total time (one value),
   Post disturbance stability time (one value)
   Second wave of balancing (one value),
   Delay in second wave (one value),
   Second balancing time (one value),
   Anticipation acuteness (graded),
   Balancing strategies (composite),
   Weight applied.

Task 1404 + 1405: Moving a gripped weight laterally and medially
*Description*:
   In result of an extension and a flexion of the arm in the elbow a weight attached to it causes a horizontal shift of the COG.
   The possibility of stepping must be provided. If the patient stands on the one leg then a wall must be near to him on the supporting side and opposite arm is free for the movement. If the patient stands in bipedal pose then he/she must be in a corner back to the camera. The space between body and wall has to be about 40 - 50 cm.
   It is convenient to belt the forearm with soft gymnastic weight about 1 - 3 kg. This weight is a parameter of monitoring.
*Options*:
   1. Right, 2. Left, 3. Reference test.
*Protocol*:
   Initial mise-en-scene:
      The patient stands in a corner, side to the wall and face or back to the camera, the arm near the wall is hanged free. The other arm is bent in the elbow and hand is close to the side of chest The distance to the wall is 35 - 40 cm.
   Camera's settings:
      Filming from the front or back. The camera axis is parallel to the coronal plane as possible. Whole body is in the frame.
   Instruction:
      Keep the balance for 3 sec and if you will feel yourself steady stretch your right {left}
      arm outside as fast as possible and keep it horizontally. Try to keep the balance in the new position for 10 sec.
      Stand in the initial position but with your right {left} arm stretched outside horizontally. Keep the balance for 3 sec and if you feel yourself steady pull your arm inside as fast as possible. Try to keep the balance for 10 sec.
      Turn 180$\bar{\circ}$
      Repeat the exercise for the second arm.
*Duration*:
   15 * 4 = 60 sec or less.
*Data registered by the operator:*
   Tasks name, options applied, options fulfilled and failure causes.
*Results obtained by the analyzer:*

45

Perturbation time (one value),
Total time (one value),
Post disturbance stability time (one value)
Second wave of balancing (one value),
Delay in second wave (one value),
Second balancing time (one value),
Anticipation acuteness (graded),
Balancing strategies (composite),
Weight applied (one value)

Tasks 1406 + 1407: COG shift caused by leg abduction and adduction
*Description*:
The perturbation is initiated by abduction and adduction (frontal lifting and lowering) of the leg.
The possibility of stepping must be provided. If the patient stands on the one leg then a wall must be near to him on the supporting side and opposite leg is free for the movement. If the patient stands in bipedal pose then he/she must be in a corner back to the camera. The space between body and wall has to be about 40 - 50 cm.
. It is possible to belt the shank with soft gymnastic weight in order to enhance the perturbation. This weight is a parameter of monitoring.
*Options*:
1. Right, 2. Left, 3.Reference test.
*Protocol*:
Initial mise-en-scene:
The patient stands in a corner, side to the wall and face or back to the camera, the arms are hanged free. The distance to the wall is 35 - 40 cm.
Camera's settings:
Filming from the front or back. The camera axis is parallel to the coronal plane as possible. Whole body is in the frame.
Instruction:
Keep the balance for 3 sec and if you will feel yourself steady lift your right {left} leg outside as fast as possible and keep it so. Try to keep the balance in the new position for 10 sec.
Stand in the initial position but with your right {left} leg lifted outside horizontally.
Keep the balance for 3 sec and if you feel yourself steady lower your leg as fast as possible. Try to keep the balance for 10 sec.
Turn 180E.
Repeat the exercise for the second leg.
*Duration*:
15 * 4 = 60 sec or less.
*Data registered by the operator:*
Tasks name, options applied, options fulfilled and failure causes.
*Results obtained by the analyzer:*
Perturbation time (one value),
Total time (one value),
Post disturbance stability time (one value)
Second wave of balancing (one value),
Delay in second wave (one value),
Second balancing time (one value),

46

Anticipation acuteness (graded),
Balancing strategies (composite),
Weight applied (one value).

TEST 15: NON MECHANICAL SELF-PERTURBATION
A head motion with eyes closed very often causes a power disturbance in balancing despite of absent of any essential mechanical pushes. It is evident that this phenomenon is associated with a cerebellum functionality and therefore should be examined.
The task with the difficulty level preceded to the difficulty level of the hardest for a given patient task is selected for an examination with a self-initiated non-mechanical perturbation.

Task 1501: Balancing with head stretched up
*Description*:
The perturbation is initiated stretching the head up with the eyes closed.
The possibility of stepping must be provided. If the patient stands on the one leg then a wall must be near to him on the supporting side and opposite leg is free for stepping. If the patient stands in bipedal pose then he/she must be in a corner back to the camera. The space between body and wall has to be about 40 - 50 cm.
*Options*:
Reference test.
*Protocol*:
Initial mise-en-scene:
The patient stands in a corner, side to the wall(-s) and face or back to the camera, the arms are hanged free. The distance to the wall(-s) is 35 - 40 cm.
Camera's settings:
Filming from the front or back. The camera axis is parallel to the coronal plane as possible. Whole body is in the frame.
Instruction:
Close your eyes.
Keep the balance for 3 sec and if you will feel yourself steady stretch your head up keep it so. Try to keep the balance in the new position for 10 sec.
*Duration*:
15 sec or less.
*Data registered by the operator:*
Task name, fulfillment and failure causes.
*Results obtained by the analyzer:*
Perturbation time (one value),
Total time (one value),
Post disturbance stability time (one value)
Second wave of balancing (one value),
Delay in second wave (one value),
Second balancing time (one value),
Anticipation acuteness (graded),
Balancing strategies (composite).

Tasks 1502 + 1503: Balancing with head thrown back and bowed
*Description*:
The perturbation is initiated by throwing back and bowing of the head.
The possibility of stepping must be provided. If the patient stands on the one leg then a wall must be near to him on the supporting side and opposite leg is free for stepping. If the patient stands in bipedal pose then he/she must be in a corner back to the camera. The space between body and wall has to be about 40 - 50 cm.

*Options*:
 1. Up, 2. Down, 3. Reference test

*Protocol*:

Initial mise-en-scene:
 The patient stands in a corner, side to the wall(-s) and face or back to the camera, the arms are hanged free. The distance to the wall(-s) is 35 - 40 cm.

Camera's settings:
 Filming from the front or back. The camera axis is parallel to the coronal plane as possible. Whole body is in the frame.

Instruction:
 Close your eyes.
 Keep the balance for 3 sec and if you will feel yourself steady throw back your head so. Try to keep the balance in the new position for 10 sec.
 Stand in the initial position. Close your eyes.
 Keep the balance for 3 sec and if you feel yourself steady bow your head as low as possible. Try to keep the balance for 10 sec.

*Duration*:
 15 * 2 = 30 sec or less.

*Data registered by the operator*:
 Tasks name, options applied, options fulfilled and failure causes.

*Results obtained by the analyzer*:
 Perturbation time (one value),
 Total time (one value),
 Post disturbance stability time (one value)
 Second wave of balancing (one value),
 Delay in second wave (one value),
 Second balancing time (one value),
 Anticipation acuteness (graded),
 Balancing strategies (composite), Tasks 1504 + 1505: Balancing with head thrown back and bowed

*Description*:
 The perturbation is initiated by turning the head clockwise and counter-clockwise. The possibility of stepping must be provided. If the patient stands on the one leg then a wall must be near to him on the supporting side and opposite leg is free for stepping. If the patient stands in bipedal pose then he/she must be in a corner back to the camera. The space between body and wall has to be about 40 - 50 cm.

*Options*:
 1. Clockwise, 2. Counter-clockwise, 3. Reference test.

*Protocol*:

Initial mise-en-scene:
 The patient stands in a corner, side to the wall(-s) and face or back to the camera, the arms are hanged free. The distance to the wall(-s) is 35 - 40 cm.

Camera's settings:
 Filming from the front or back. The camera axis is parallel to the coronal plane as possible. Whole body is in the frame.

*Instruction*:
Close your eyes.
Keep the balance for 3 sec and if you will feel yourself steady turn your head clockwise up to end and keep it so. Try to keep the balance in the new position for 10 sec.
Stand in the initial position. Close your eyes.
Keep the balance for 3 sec and if you feel yourself steady turn your head counter-clockwise up to end and keep it so. Try to keep the balance for 10 sec.
*Duration*:
15 * 2 = 30 sec or less.
*Data registered by the operator*:
Tasks name, options applied, options fulfilled and failure causes.
*Results obtained by the analyzer*:
Perturbation time (one value),
Total time (one value),
Post disturbance stability time (one value)
Second wave of balancing (one value),
Delay in second wave (one value),
Second balancing time (one value),
Anticipation acuteness (graded),
Balancing strategies (composite), TEST 16: FREE WALKING
Free level walking and walking in place are associated with balancing in motion when various dynamic perturbations as expected as well as random accompany the steady locomotion. Resistance to these perturbations is examined so. Such features as clearance, velocity, width of the base and especially its stability, characterize the capacity to adapt to an environment conditions. Limp and other distortions of normal gait pattern are associated with musculoskeletal and nervous disorders.

Task 1601: Free level walking
*Description*:
Usually in home only short "walkway" (about 3 - 4 m long) is available. But due to a fact that in elderly the stride is rather shortened (100 cm or less) the central part of the "walkway" corresponds to steady walking and includes a full stride. To obtain minimal statistics 10 - 15 trials have to be carried out.
On the other hand, only central part about 1.5 m is suitable enough for accurate enough image processing of records obtained by a single camera.
It is very desirable to mark the center of the "walkway".
*Options*:
None.
*Protocol*:
Initial mise-en-scene:
The patient stands as straight as possible at a center of the "walkway" face to the camera for recording of his/her static pose. Then he/she turns side and back to the camera. So the three views of the posture are obtained and camera is tuned.
Then the patient stands on a left edge of the "walkway" preparing to start with the certain leg. The leg is selected so that the patient will come in to the central zone with his/her right leg.

When the patient is on the opposite edge he/she starts so that to come in to the
central zone with the left leg.
Camera's settings:
Filming from the side. The camera axis is perpendicular to the "walkway". Whole
body is in the frame. The zoom is widest. Shutter is 100 or more. Iris is full and gain
is tuned accordingly to the illumination.
Instruction:
{After recording of standing at the center of "walkway"}.
Go with your right {left} leg. At the opposite end turn back and start with your right
{left} leg.
Make 10 trials.
*Duration*:
6 * 10 = 60 sec or more.
*Data registered by the operator:*
Task name, fulfillment and failure causes.
*Results obtained by the analyzer:*
Posture: Lumbar lordosis (graded),
Scoliosis (graded),
Stoop (graded),
Thoracic kyphosis (graded),
Posture distortion grade (graded).
Gate: Orthopaedic aid (composite),
Instability signs (composite),
Loss of balance events (one value),
Failures (one value),
Sudden stop (one value),
Gait patterns (composite),
Gait disorders (composite),
Side involved (composite),
Velocity (one value),
Clearance, right (graded),
Clearance, left (graded),
Arm-leg asynergia, right (one value),
Arm-leg asynergia, left (one value),
Cycle duration (one value),
Cycle variance (one value),
Single support, right (one value),
Single support, left (one value),
Single support variance, right (one value),
Single support variance, left (one value),
Double support, right ahead (one value),
Double support, left ahead (one value),
Step length, right (one value),
Step length, left (one value),
Step length variance, right (one value),
Step length variance, left (one value),
Base width (one value),
Base variance, left to right (one value),
Base variance, right to left (one value), Foot to floor angle at middle swing, right (one value),
Foot to floor angle at middle swing, left (one value),
Foot to floor angle at terminal swing, right (one value),
Foot to floor angle at terminal swing, left (one value),
Foot to floor angle at initial contact, right (one value),
Foot to floor angle at initial contact, right (one value).

Task 1602: Free walking in place
*Description*:
For estimation of stability in walking it is very important the front and rear views of a walking subject. But usually in home only short "walkway" (about 3 - 4 m long) in one direction is available. Hence with help of a single camera one can examine only one of two acceptable views (sagittal and frontal). For stability assessment is preferable to use a sagittal view for examination of a locomotion (progression) and a frontal view for walking in place. This exercise gives almost all features of balancing in motion and a powerful statistics, about 100 steps or more.
Before accomplishment of walking in place the patient stands as straight as possible at a center of the "walkway" face to the camera for recording of his/her static pose. Then he/she turns side and back to the camera. So the three views of the posture are obtained and camera is tuned.
It is very desirable to mark the center of the "walkway" where the posture recording and walking in place should be performed.
*Options*:
1. Front, 2. Back
*Protocol*:
Initial mise-en-scene:
The patient stands as straight as possible at a center of the "walkway" face to the camera for recording of his/her static pose. Then he/she turns side and back to the camera. So the three views of the posture are obtained and camera is tuned.
Then the patient stands at the same place preparing to start walking in place.
Camera's settings:
Filming from the face {back}. The camera axis is perpendicular to the "walkway". Whole body is in the frame. Shutter is 100 or more. Iris is full and gain is tuned accordingly to the illumination.
Instruction:
{After recording of standing at the center of "walkway"}.
Walk in place with your own pace for one minute.
Turn 180E. Repeat the exercise.
*Duration*:
60 * 2 = 120 sec or more.
*Data registered by the operator:*
Task name, options applied, options fulfilled and failure causes.
*Results obtained by the analyzer:*
Posture: Lumbar lordosis (graded),
Scoliosis (graded),
Stoop (graded),
Thoracic kyphosis (graded),
Posture distortion grade (graded).
Gait: Orthopaedic aid (composite), Side involved (composite),
Instability signs (composite),
Loss of balance events (one value),
Failures (one value),
Sudden stop (one value),
Gait patterns (composite),
Gait disorders (composite),
Side involved (composite),
Clearance, right (graded),
Clearance, left (graded),
Arm-leg asynergia, right (one value),
Arm-leg asynergia, left (one value),
Cycle duration (one value),
Cycle variance (one value),
Single support, right (one value),
Single support, left (one value),
Single support variance, right (one value),
Single support variance, left (one value),
Double support, right ahead (one value),
Double support, left ahead (one value),
Base width (one value),
Base variance, left to right (one value),
Base variance, right to left (one value),
Foot progression, right (graded),
Foot progression, left (graded).

TEST 17: COMPLICATED WALKING
Steady walking with irregular options reveals an ability of a patient to adapt to new circumstances and/or learn a new stereotype. The conditions for balancing are more complicated and so hidden disorders in motor control of the whole body could be detected.

Task 1701: Free walking in place with eyes closed
*Description*:
The task checks the capacity to conserve a position while relatively simple and automatic movements are performing without visual support. Also balancing in frontal plane and synergy can be assessed.
The operator stops the patient by command if he/she has wandered too near to an obstacle..
A large statistics may be obtained in this task.
*Options*:
1. Front, 2. Back.
*Protocol*:
Initial mise-en-scene:
The patients stands on the "walkway" opposite to the camera, face or back to it.
His/her coronal plane is directed along the "walkway".
Camera's settings:
Filming from the front or back. The camera axis is perpendicular to the "walkway". Whole body is in the frame. The zoom is widest. Shutter is 100 or more. Iris is full and gain is tuned accordingly to the illumination.

Instruction:
   Close your eyes. Walk in place for 30 sec. Stop immediately when I command you
   " to Stop!"
   Turn 180E and do the same exercise.
Duration:
   30 * 2 = 60 sec.
Data registered by the operator:
   Tasks name, options applied, options fulfilled and failure causes.
Results obtained by the analyzer:
   Orthopedic aid (composite),
   Side involved (composite),
   Performance quality (graded),
   Instability signs (composite),
   Loss of balance events (one value),
   Failures (one value),
   Sudden stop (one value),
   Balancing strategies (composite),
   Cycle duration (one value),
   Cycle variance (one value),
   Clearance, right (graded),
   Clearance, left (graded),
   Deviation to Right (one value),
   Deviation to Left (one value).

Task 1702: Free level walking with eyes closed

Description:
The task checks the capacity to keep a direction while walking without visual support.
Also a lack in automation and balancing problems can be revealed.
The operator stops walking by command if an obstacle or a wall will be too near.
Options:
   None.
Protocol:
   Initial mise-en-scene:
      The patient makes 1 - 2 trials with the eyes opened to set a reference points for the
      direction of walking and to estimate boundaries of the "walkway". Then he/she
      stands one end of the "walkway" in order to start with the closed eyes.
   Camera's settings:
      Filming from the side. The camera axis is perpendicular to the "walkway". Whole
      body is in the frame. The zoom is widest. Shutter is 100 or more. Iris is full and gain
      is tuned accordingly to the illumination.
   Instruction:
      Close your eyes. Go to next end stop there and open your eyes. Stop immediately
      if I shell command you "Stop!"
      Do the same in opposite direction.
Duration:
   5 * 2 = 10 sec or more.
Data registered by the operator:
   Task name, fulfillment and failure causes.
Results obtained by the analyzer:

Orthopedic aid (composite),
Side involved (composite),
Performance quality (graded),
Instability signs (composite),
Loss of balance events (one value),
Failures (one value),
Sudden stop (one value),
Balancing strategies (composite),
Velocity (one value),
Clearance, right (graded),
Clearance, left (graded),
Deviation to Right (one value),
Deviation to Left (one value).

Task 1703: Walking a line with normal step length
*Description*:
Walking with extremely narrow base checks an ability to keep the direction and balance, especially with the eyes closed. Also, high level disorders such as apraxia, fear, abrupt stop and freezing may appear.
*Options*:
1. Eyes opened, 2.Eyes closed.
*Protocol*:
Initial mise-en-scene:
The patients stands at the one end of the "walkway" with his/her sagittal plane along it.
Camera's settings:
Filming from the side. The camera axis is perpendicular to the "walkway". Whole body is in the frame. The zoom is widest. Shutter is 100 or more. Iris is full and gain is tuned accordingly to the illumination.
Instruction:
{Close your eyes}. Walk a line with arbitrary velocity. Keep the direction. {Stop immediately when I command you "to Stop!"}
Turn 180E and do the same exercise.
*Duration*:
7 * 2 = 15 sec or more.
*Data registered by the operator:*
Tasks name, options applied, options fulfilled and failure causes.
*Results obtained by the analyzer:*
Orthopedic aid (composite),
Side involved (composite),
Performance quality (graded),
Instability signs (composite),
Loss of balance events (one value),
Failures (one value),
Sudden stop (one value),
Balancing strategies (composite),
Quickness (one value),
Deviation to Right (one value),
Deviation to Left (one value).

Task 1704: Walking a line with arms folded and with normal step length
*Description*:
Walking with extremely narrow base checks an ability to keep the direction and balance, especially with the eyes closed. Folding the arms makes balancing more difficult.
Also, high level disorders such as apraxia, fear, abrupt stop and freezing may appear.
*Options*:
1. Eyes opened, 2. Eyes closed.
*Protocol*:
Initial mise-en-scene:
The patients stands at the one end of the "walkway" with arms folded on the chest. His/her sagittal plane is directed along the "walkway".
Camera's settings:
Filming from the side. The camera axis is perpendicular to the "walkway". Whole body is in the frame. The zoom is widest. Shutter is 100 or more. Iris is full and gain is tuned accordingly to the illumination.
Instruction:
{Close your eyes}. Walk a line with arbitrary velocity. Keep the direction. {Stop immediately when I command you "to Stop!"}
Turn 180E and do the same exercise.
*Duration*:
7 * 2 = 15 sec or more.
*Data registered by the operator:*
Tasks name, options applied, options fulfilled and failure causes.
*Results obtained by the analyzer:*
Orthopedic aid (composite),
Side involved (composite),
Performance quality (graded),
Instability signs (composite),
Loss of balance events (one value),
Failures (one value),
Sudden stop (one value),
Balancing strategies (composite),
Quickness (one value),
Deviation to Right (one value),
Deviation to Left (one value).

Task 1705: Tandem walking
*Description*:
Tandem walking is walking a line with a shortest steps length (a heel of the front leg is just after a forefoot of the rear leg). That is a complicated option of the task "Walking a line with normal step length" and checks the same features.
*Options*:
1. Eyes opened, 2. Eyes closed.
*Protocol*:
Initial mise-en-scene:
The patients stands in tandem pose at the one end of the "walkway". His/her sagittal plane is directed along the "walkway".

Camera's settings:
Filming from the side. The camera axis is perpendicular to the "walkway".
Whole body is in the frame. The zoom is widest. Shutter is 100 or more. Iris is full
and gain is tuned accordingly to the illumination.

Instruction:
{Close your eyes}. Walk a line with arbitrary velocity. Keep the direction. {Stop
immediately when I command you "to Stop!"}
Turn 180E and do the same exercise.

*Duration*:
15 * 2 = 30 sec or more.

*Data registered by the operator*:
Tasks name, options applied, options fulfilled and failure causes.

*Results obtained by the analyzer*:
Orthopedic aid (composite),
Side involved (composite),
Performance quality (graded),
Instability signs (composite),
Loss of balance events (one value),
Failures (one value),
Sudden stop (one value),
Balancing strategies (composite),
Quickness (one value),
Deviation to Right (one value),
Deviation to Left (one value).

TEST 18: MANEUVERS
The test checks an ability of a voluntary changing of an initial steady locomotion.

Task 1801 + 1803: Ignition of walking and Abrupt stop

*Description*:
The time between an intention to go and the real implementation is defined as delay
in starting of walking after the command "Go!". The number of steps made by the
patient after the command "Stop!" characterize his/her ability to interrupt a steady
motion.

*Options*:
None.

*Protocol*:
Initial mise-en-scene:
The patients stands at the end of the "walkway" so to be visible to the camera.
His/her sagittal plane is directed along the "walkway".

Camera's settings:
Filming from the side. The camera axis is perpendicular to the "walkway".
Whole body is in the frame. The zoom is widest. Shutter is 100 or more. Iris is full
and gain is tuned accordingly to the illumination.

Instruction:
Go! [When the patient achieves a center of the "walkway" to give the next command]
Stop!
Go to the end. Turn 180E. Move a little to be visible. [Repeat the exercise].

*Duration*:

10 * 2 = 20 sec or more.
*Data registered by the operator:*
    Tasks name, fulfillment and failure causes.
*Results obtained by the analyzer:*
    Orthopedic aid (composite),
    Side involved (composite),
    Task 1801:
        Ignition delay (one value).
    Task 1803:
    Performance quality (graded),
    Instability signs (composite),
    Loss of balance events (one value),
    Balancing strategies (composite),
    Number of steps to stop (one value).

Task 1802: Changing speed
*Description*:
    The task checks an ability to decrease the speed voluntary.
*Options*:
    None.
*Protocol*:
    Initial mise-en-scene:
        The patients stands at the end of the "walkway". His/her sagittal plane is directed
        along the "walkway".
    Camera's settings:
        Filming from the side. The camera axis is perpendicular to the "walkway".
        Whole body is in the frame. The zoom is widest. Shutter is 100 or more. Iris is full
        and gain is tuned accordingly to the illumination.
    Instruction:
        Go! [After two-three steps to give the next command]. Go slowly!
        [At the end of the "walkway"] Turn 180E! [Repeat the exercise in opposite direction].
        Go to the end. Turn 180E. Move a little to be visible. [Repeat the exercise].
    Duration:
        10 * 2 = 20 sec or more.
*Data registered by the operator:*
    Task name, fulfillment and failure causes.
*Results obtained by the analyzer:*
    Orthopedic aid (composite),
    Side involved (composite),
    Performance quality (graded),
    Instability signs (composite),
    Loss of balance events (one value),
    Sudden stop (one value),
    Balancing strategies (composite),
    Number of steps to decelerate (one value).

Task 1804 + 1906: Stepping around an obstacle
*Description*:
    The task 1804 checks an ability to adapt the direction and speed to external conditions.

The task 1906 relates to the test: "Single motor task". It checks an ability to start and perform an isolated motor stereotype.

Implementation of the both tasks is associated with a risk of "freezing" and/or dizziness. The rout of the patient is organized so that he/she is near a support while going around and turning, e.g. he/she goes between camera and the obstacle and turns to the wall after the obstacle, passes between the obstacle and the wall and stops after one - two steps. Then he/she do the task 1906 (turn 180E) beginning to revolve by his face to the wall and so having the possibility to support during all the time.

*Options*:
1. Clockwise, 2. Counter-clockwise.

*Protocol*:

Initial mise-en-scene:
The patients stands at the end of the "walkway". His/her sagittal plane is directed along the "walkway". An obstacle (a chair, walker or quad cane) stands at the center of the "walkway" a meter apart from a wall. If the "walkway" is a diagonal of the room it is required to reserve .2 m in the other place near a wall inside a field of view of the camera.

Camera's settings:
It is preferable but not necessary to film from the side.
Whole body is in the frame. The zoom is widest. Shutter is 100 or more. Iris is full and gain is tuned accordingly to the illumination.

Instruction:
Go around the obstacle by the following way: from the camera to the wall, between the obstacle and the wall and turn a little from the wall to a central line of the "walkway", make 1 - 2 steps and stop.
Turn 180E revolving to the wall.
[Repeat the exercise in opposite direction].

*Duration*:
10 * 2 = 20 sec or more.

*Data registered by the operator:*
Tasks name, options applied, options fulfilled and failure causes.

*Results obtained by the analyzer:*
Tasks 1804 and 1906:
Orthopedic aid (composite),
Side involved (composite),
Performance quality (graded),
Instability signs (composite),
Loss of balance events (one value),
Balancing strategies (composite),
Task 1804:
Sudden stop (one value),
Manner of going around (composite),
Number of steps to go around (one value),
Duration (one value).
Task 1906:
Number of steps to turn (one value),
Duration (one value).

58

WO 01/88836 PCT/US01/16180

Task 1805: Stepping on drawn or appearing targets
  *Description*:
    The task checks an ability to control the whole body in motion.
    The targets are rectangular drawn on a carpet (floor) or a light spot appearing in front of the patients. He/she tries to tread on the targets while walking. The number of the hits and quickness of performing are assessed. Also the secondary events of a balance loss may occur.
  *Options*:
    None.
  *Protocol*:
    Initial mise-en-scene:
      The patients stands at the end of the "walkway". His/her sagittal plane is directed along the "walkway".
    Camera's settings:
      Filming from the side. The camera axis is perpendicular to the "walkway". Whole body is in the frame. The zoom is widest. Shutter is 100 or more. Iris is full and gain is tuned accordingly to the illumination.
    Instruction:
      Go, try to step on targets.
      [At the end]. Turn 180E. [Repeat the exercise in opposite direction].
    Duration:
      10 * 2 = 20 sec or more.
  *Data registered by the operator:*
    Task name, fulfillment and failure causes.
  *Results obtained by the analyzer:*
    Orthopedic aid (composite),
    Side involved (composite),
    Performance quality (graded),
    Instability signs (composite),
    Loss of balance events (one value),
    Sudden stop (one value),
    Balancing strategies (composite),
    Quickness (one value),
    Hitting quality, Right (one value),
    Hitting quality, Left (one value).

TEST 19: SINGLE MOTOR TASK
  A human nervous system and locomotor apparatus deal with unsteady transient processes while performing a single motor task. This condition helps to reveal additional disorders to those that manifested themselves in the examinations of a steady motion.

Task 1901: Romberg with arms stretched forward
  *Description*:
    The task checks presence of tremor without the visual support.
  *Options*:
    None.
  *Protocol*:
    Initial mise-en-scene:

59

The patients stands on the "walkway", the face to the camera and his/her coronal plane is perpendicular to the camera axis.
Camera's settings:
Filming from the front. The camera axis is perpendicular to the coronal plane of the patient. Zoom in on the patient's upper body but so that his/her stretched out arms and fingers were in the frame. The fingers must be in the focus.
Instruction:
Close your eyes. Stretch your arms and palms forward and aside a little. Try to stand so for 30 sec.
Do this exercise twice.
Duration:
30 * 2 = 60 sec or less.
Data registered by the operator:
Task name, fulfillment and failure causes.
Results obtained by the analyzer:
Balancing strategies (composite),
Tremor amplitude, hand, Right (one value),
Tremor amplitude, hand, Left (one value),
Tremor frequency, hand, Right (one value),
Tremor frequency, hand, Left (one value), Task 1902: Looking behind with the trunk twisting
Description:
The task checks an ability to make voluntary a relatively seldom set of motions: looking over the shoulder as behind as possible with maximal twisting of the trunk. This task is a combination of a simple aim and some muscle efforts to reach it. Also the secondary events of a balance loss, such as dizziness, may occur.
Options:
1. Clockwise, 2. Counter-clockwise.
Protocol:
Initial mise-en-scene:
The patients stands in the corner, back to the camera.
Camera's settings:
Filming from the back. The camera axis is perpendicular to the coronal plane as possible. Whole body is in the frame.
Instruction:
Try to look in to the camera over your Right shoulder. Keep so for a second. Back to initial pose. Do the same over your Left shoulder.
Duration:
5 * 2 = 10 sec or more.
Data registered by the operator:
Task name, options applied, options fulfilled and failure causes.
Results obtained by the analyzer:
Performance quality (graded),
Instability signs (composite),
Balancing strategies (composite),
Duration (one value),
Ignition delay (one value).

Task 1903: Walking sidewise
   *Description*:
      The task checks an ability to start and to walk by a rather unusual way.
      Also the secondary events of a balance loss may occur.
   *Options*:
      1. Right, 2. Left.
   *Protocol*:
      Initial mise-en-scene:
         The patients stands at the end of the "walkway". His/her coronal plane is directed along the "walkway".
      Camera's settings:
         Filming from the back. The camera axis is perpendicular to the "walkway". Whole body is in the frame. The zoom is widest. Shutter is 100 or more. Iris is full and gain is tuned accordingly to the illumination.
      Instruction:
         Walk sidewise without crossing your legs.
         [At the end]. Walk in the opposite direction.
         [Repeat the exercise twice].
   *Duration*:
      5 * 4 = 20 sec or more.
   *Data registered by the operator:*
      Task name, options applied, options fulfilled and failure causes.
   *Results obtained by the analyzer:*
      Orthopedic aid (composite),
      Side involved (composite),
      Performance quality (graded),
      Instability signs (composite),
      Loss of balance events (one value),
      Sudden stop (one value),
      Balancing strategies (composite),
      Ignition delay (one value),
      Quickness (one value),
      Abduction (one-value).

Task 1904: Walking sidewise with a scissors like movements
   *Description*:
      The task checks an ability to start and to walk by an unusual way with a rather fine coordination of the legs. The task is associated with some risk to fall and has to be carried out near a wall.
      The secondary events of a balance loss may occur.
   *Options*:
      1. Right, 2. Left.
   *Protocol*:
      Initial mise-en-scene:
         The patients stands at the end of the "walkway". His/her coronal plane is directed along the "walkway". One leg must be in front of the other in order to prevent catching one foot with other leg.
      Camera's settings:
         Filming from the back. The camera axis is perpendicular to the "walkway".

Whole body is in the frame. The zoom is widest. Shutter is 100 or more. Iris is full
and gain is tuned accordingly to the illumination.
Instruction:
Walk sidewise crossing your legs.
[At the end]. Walk in the opposite direction. Try to change the leading leg.
Duration:
7 * 2 = 15 sec or more.
*Data registered by the operator:*
Task name, options applied, options fulfilled and failure causes.
*Results obtained by the analyzer:*
Orthopedic aid (composite),
Side involved (composite),
Performance quality (graded),
Instability signs (composite),
Loss of balance events (one value),
Sudden stop (one value),
Balancing strategies (composite),
Ignition delay (one value),
Quickness (one value),
Abduction (one-value),
Adduction (one value).

Task 1905: Sitting to standing and vise versa
*Description:*
The task checks the ability to stand up and sit down without help of hands. Also
lowering of the blood pressure at standing and balancing just after standing may be
evaluated.
*Options:*
1. Up, 2. Down.
*Protocol:*
Initial mise-en-scene:
The patients sits in the armchair with his/her feet tightly supported by the floor. He/
she can to bend so that the COG comes into the supporting area in order to stand
up without help of the arms. Simultaneously, patient's weight and blood pressure
may be measured.
Camera's settings:
Filming from the front. The camera axis is perpendicular to a coronal plane of
the patient. Whole body is in the frame when he/she is standing.
Instruction:
Try stand up without help of your arms.
Stand for a minute in order to measure your blood pressure.
Try to sit down without help of your arms.
Duration:
3 * 2 + 60 = 65 sec or more.
*Data registered by the operator:*
Task name, options applied, options fulfilled and failure causes.
*Results obtained by the analyzer:*
Orthopedic aid (composite),
Side involved (composite), Performance quality (graded),
Instability signs (composite),
Balancing strategies (composite),
Ignition delay (one value),
Sitting down quickness (one value),
Standing up quickness (one value),
Preparation time (one value),
Support grade (graded),
Right/Left division of the support (graded)

Task 1905: Turn 180E (The task is combined with Task 1804)

TEST 20: TWO MOTOR TASK TOGETHER
The test checks an ability to coordinate implementation of two different motor tasks simultaneously. That relates to more specific properties of the central nervous system than in the case of implementation of a single task.

Task 2001: Shaking an imaginary hand when standing
*Description*:
   The task checks the ability to stand up and do something different in the same time.
   The patient rises from an armchair and tries to shank an imaginary hand of a friend.
*Options*:
   None.
*Protocol*:
   Initial mise-en-scene:
      The patients sits in the armchair with his/her feet tightly supported by the floor. He/she can to bend so that the COG comes into the supporting area in order to stand up without help of the arms. Simultaneously, patient's weight may be measured.
   Camera's settings:
      Filming from the front. The camera axis is perpendicular to a coronal plane of the patient. Whole body is in the frame when he/she is standing.
   Instruction:
      Try stand up without help of your arms and to shake a hand of yours imaginary friend.
      [If OK]. Sit down please.
      [If not OK] Try to do this with support. [If OK] Sit down please.
      [Repeat the task 3 times].
   Duration:
      5 * 3 = 15 sec or more.
*Data registered by the operator:*
   Task name, fulfillment and failure causes.
*Results obtained by the analyzer:*
   Orthopedic aid (composite),
   Side involved (composite),
   Performance quality (graded),
   Instability signs (composite),
   Balancing strategies (composite),
   Ignition delay (one value),
   Preparation time (one value), Support grade (graded),
Fall into armchair (one value)

Task 2002: Gazing into the camera while walking
  *Description*:
    The task checks the ability to walk and do something different in the same time.
    The patient walks by "walkway" and gaze into the camera that stands aside.
  *Options*:
    1. Right, 2. Left.
  *Protocol*:
    Initial mise-en-scene:
      The patients stands at the end of the "walkway". His/her sagittal plane is directed along the "walkway".
    Camera's settings:
      Filming from the side. The camera axis is perpendicular to the "walkway".
      Whole body is in the frame. The zoom is widest. Shutter is 100 or more. Iris is full and gain is tuned accordingly to the illumination.
    Instruction:
      Try to gaze into the camera while walking forward and backward.
  *Duration*:
    5 * 2 = 10 sec or more.
  *Data registered by the operator:*
    Task name, options applied, options fulfilled and failure causes.
  *Results obtained by the analyzer:*
    Performance quality (graded),
    Loss of balance events (one value),
    Instability signs (composite),
    Balancing strategies (composite),
    Sudden stop (one value),
    Gazing features (composite),
    Gazing quality (graded),
    Duration (one value)

WO 01/88836　　　　　　　　　　　　　　　　　　　　　　　　　　PCT/US01/16180

APPENDIX C

ONE VALUE RESULTS

|  | Name | Units | Data type |
|---|---|---|---|
| 1 | None |  | null |
| 2 | Abduction | degrees | integer |
| 3 | Active pelvic obliquity | degrees | integer |
| 4 | Adduction | degrees | integer |
| 5 | Applied weight | kg | float |
| 6 | Arm-Leg asynergia, Left | % of cycle | integer |
| 7 | Arm-Leg asynergia, Right | % of cycle | integer |
| 8 | Balancing time | sec | integer |
| 9 | Base variance, Left | % | integer |
| 10 | Base variance, Right | % | integer |
| 11 | Base width | % of ref. base | integer |
| 12 | Cane_ tip-toe base | % of ref. base | integer |
| 13 | Cane to feet distance | % of foot length | integer |
| 14 | Cycle duration | sec | float |
| 15 | Cycle variance | % | integer |
| 16 | Delay in second wave | sec | integer |
| 17 | Deviation to Left | % of ref. base | integer |
| 18 | Deviation to Right | % of ref. base | integer |
| 19 | Diastolic Blood Pressure | mm Hg | integer |
| 20 | Dorsiflexion | degrees | integer |
| 21 | Duration | sec | integer |
| 22 | Double support, Left ahead | % of cycle | integer |
| 23 | Double support, Right ahead | % of cycle | integer |
| 24 | Exposure time | sec | integer |
| 25 | Failures | % of steps | integer |
| 26 | Fall into armchair |  | boolean |
| 27 | Foot _Tip-toe base | % of ref. base | integer |
| 28 | Foot to floor angle at Init. Cont. | degrees | integer |
| 29 | Foot to floor angle at Mid. Sw. | degrees | integer |
| 30 | Foot to fl. ang. before Term. Sw. | degrees | integer |
| 31 | Further normalization |  | boolean |
| 32 | Heart Rate gain | % | integer |
| 33 | Heel off, Left | % of cycle | integer |
| 34 | Heel off, Right | % of cycle | integer |
| 35 | Hip abduction | degrees | integer |
| 36 | Hip adduction | degrees | integer |
| 37 | Hip extension | degrees | integer |
| 38 | Hip flexion | degrees | integer |
| 39 | Hitting quality, Left | hits/steps | float |
| 40 | Hitting quality, Right | hits/steps | float |
| 41 | Ignition delay | sec | integer |
| 42 | Knee flexion | degrees | integer |
| 43 | Knee extension | degrees | integer |
| 44 | Loss of balance events | % of steps | integer |

| | | | | |
|---|---|---|---|---|
| | 45 | Number of steps to go around | | integer |
| | 46 | Number of steps to stop | | integer |
| | 47 | Number of steps to turn | | integer |
| | 48 | Number of step to decelerate | | |
| | 49 | Nystagmus | | boolean |
| | 50 | O-ring touching quickness | touches/sec | float |
| | 51 | Pelvic obliquity | degrees | integer |
| | 52 | Perturbation time | sec | float |
| | 53 | Post disturbance stability time | sec | integer |
| | 54 | Preparation time | sec | integer |
| | 55 | Quickness | step/sec | float |
| | 56 | Reach lateral | % of ref. base | float |
| | 57 | Reach sagittal | % of support area length | float |
| | 58 | Second balancing time | sec | integer |
| | 59 | Second wave of balancing | | boolean |
| | 60 | Single support, Left | % of cycle | integer |
| | 61 | Single support, Right | % of cycle | integer |
| | 62 | Single support variance, Left | % | integer |
| | 63 | Single support variance, Right | % | integer |
| | 64 | Sitting down quickness | sec | float |
| | 65 | Slow descending time | sec | integer |
| | 66 | Slow lifting time | sec | integer |
| | 67 | Standing up quickness | sec | float |
| | 68 | Step length, Left | % of foot length | integer |
| | 69 | Step length, Left Variance | % | integer |
| | 70 | Step length, Right | % of foot length | integer |
| | 71 | Step length, Right Variance | % | integer |
| | 72 | Step width, Left | % of ref. base | integer |
| | 73 | Step width, Left Variance | % | integer |
| | 74 | Step width, Right | % of ref. base | integer |
| | 75 | Step width, Right Variance | % | integer |
| | 76 | Stride length | m | float |
| | 77 | Successful attempts | hits/attempts | float |
| | 78 | Sudden stop | % of trials | integer |
| | 79 | Sway frontal, Left | % of ref. base | integer |
| | 80 | Sway frontal, Right | % of ref. base | integer |
| | 81 | Sway sagittal, Left | % of foot length | integer |
| | 82 | Sway sagittal, Right | % of foot length | integer |
| | 83 | Systolic Blood Pressure | mm Hg | integer |
| | 84 | Total time of balancing | sec | integer |
| | 85 | Tremor amplitude,foot,Left | cm | float |
| | 86 | Tremor amplitude,foot,Right | cm | float |
| | 87 | Tremor amplitude,hand,Left | cm | float |
| | 88 | Tremor amplitude,hand,Right | cm | float |
| | 89 | Tremor frequency,foot,Left | Hz | integer |
| | 90 | Tremor frequency,foot,Right | Hz | integer |
| | 91 | Tremor frequency,hand,Left | Hz | integer |
| | 92 | Tremor frequency,hand,Right | Hz | integer |
| | 93 | Two tip-toes base | % of ref./ base | integer |

| 94 | Velocity | km/h | float |

APPENDIX D

GRADED RESULTS

| ID | Name |
|---|---|
| 1 | Null |
| 2 | Anticipation reaction acuteness |
| 3 | Bag under eye |
| 4 | Clearance, Left side |
| 5 | Clearance, Right side |
| 6 | Dorsiflexion loading grade |
| 7 | Face asymmetry |
| 8 | Foot progression, Left |
| 9 | Foot progression, Right |
| 10 | Foot pronation |
| 11 | Foot supination |
| 12 | Gazing quality |
| 13 | Gluteus medius strength |
| 15 | Hip rotation, external |
| 16 | Hip rotation, internal |
| 17 | Lumbar lordosis |
| 18 | Neck bending |
| 19 | Neck twisting |
| 20 | Performance quality |
| 21 | Posture distortion grade |
| 22 | Posture evolution |
| 23 | Pupil reactions |
| 24 | Range of Motion grade |
| 25 | Restrictions in looking behind |
| 26 | Right/Left ratio of the support |
| 27 | Scoliosis |
| 28 | Stoop |
| 29 | Support grade |
| 30 | Thoracic kyphosis |
| 31 | Trunk bending |
| 32 | Trunk twisting |

GRADED_SCALES

| | Name | Scale | Data type |
|---|---|---|---|
| 1 | Anticipation reaction acuteness | adequate | string |
| 2 | Anticipation reaction acuteness | moderate | string |
| 3 | Anticipation reaction acuteness | mild | string |
| 4 | Anticipation reaction acuteness | none | string |
| 5 | Bag under eye | none | string |
| 6 | Bag under eye | small | string |
| 7 | Bag under eye | moderate | string |
| 8 | Bag under eye | large | string |
| 9 | Clearance, Left side | excessive | string |
| 10 | Clearance, Left side | normal | string |

WO 01/88836     PCT/US01/16180

| | | | | |
|---|---|---|---|---|
| | 11 | Clearance, Left side | reduced | string |
| | 12 | Clearance, Left side | mild | string |
| | 13 | Clearance, Left side | absent | string |
| | 14 | Clearance, Right side | excessive | string |
| 5 | 15 | Clearance, Right side | normal | string |
| | 16 | Clearance, Right side | reduced | string |
| | 17 | Clearance, Right side | mild | string |
| | 18 | Clearance, Right side | absent | string |
| | 19 | Dorsiflexion loading grade | full | string |
| 10 | 20 | Dorsiflexion loading grade | moderate | string |
| | 21 | Dorsiflexion loading grade | mild | string |
| | 22 | Dorsiflexion loading grade | none | string |
| | 23 | Face asymmetry | none | string |
| | 24 | Face asymmetry | slight | string |
| 15 | 25 | Face asymmetry | evident | string |
| | 26 | Face asymmetry | severe | string |
| | 27 | Foot progression, Left | normal | string |
| | 28 | Foot progression, Left | too external | string |
| | 29 | Foot progression, Left | too internal | string |
| 20 | 30 | Foot progression, Right | normal | string |
| | 31 | Foot progression, Right | too external | string |
| | 32 | Foot progression, Right | too internal | string |
| | 33 | Foot pronation | full | string |
| | 34 | Foot pronation | reduced | string |
| 25 | 35 | Foot pronation | mild | string |
| | 36 | Foot pronation | absent | string |
| | 37 | Foot supination | full | string |
| | 38 | Foot supination | reduced | string |
| | 39 | Foot supination | mild | string |
| 30 | 40 | Foot supination | absent | string |
| | 41 | Gazing quality | good | string |
| | 42 | Gazing quality | moderate | string |
| | 43 | Gazing quality | low | string |
| | 44 | Gazing quality | bad | string |
| 35 | 45 | Gluteus medius strength | adequate | string |
| | 46 | Gluteus medius strength | moderate | string |
| | 47 | Gluteus medius strength | reduced | string |
| | 48 | Gluteus medius strength | none | string |
| | 49 | Hip rotation, external | excessive | string |
| 40 | 50 | Hip rotation, external | adequate | string |
| | 51 | Hip rotation, external | reduced | string |
| | 53 | Hip rotation, external | mild | string |
| | 54 | Hip rotation, external | none | string |
| | 55 | Hip rotation, internal | excessive | string |
| 45 | 56 | Hip rotation, internal | adequate | string |
| | 57 | Hip rotation, internal | reduced | string |
| | 58 | Hip rotation, internal | mild | string |
| | 59 | Hip rotation, internal | none | string |
| | 60 | Lumbar lordosis | absent | string |

| | | | | |
|---|---|---|---|---|
| | 61 | Lumbar lordosis | mild | string |
| | 62 | Lumbar lordosis | moderate | string |
| | 63 | Lumbar lordosis | severe | string |
| | 64 | Neck bending | excessive | string |
| 5 | 65 | Neck bending | adequate | string |
| | 66 | Neck bending | reduced | string |
| | 67 | Neck bending | mild | string |
| | 68 | Neck bending | none | string |
| | 69 | Neck twisting | excessive | string |
| 10 | 70 | Neck twisting | adequate | string |
| | 71 | Neck twisting | reduced | string |
| | 72 | Neck twisting | mild | string |
| | 73 | Neck twisting | none | string |
| | 74 | Performance quality | confident | string |
| 15 | 75 | Performance quality | unsure | string |
| | 76 | Performance quality | erroneous | string |
| | 77 | Performance quality | disable | string |
| | 78 | Posture distortion | absent | string |
| | 79 | Posture distortion | mild | string |
| 20 | 80 | Posture distortion | moderate | string |
| | 81 | Posture distortion | severe | string |
| | 82 | Posture evolution | much better | string |
| | 83 | Posture evolution | better | string |
| | 84 | Posture evolution | the same | string |
| 25 | 85 | Posture evolution | worse | string |
| | 86 | Posture evolution | much worse | string |
| | 87 | Posture evolution | very bad | string |
| | 88 | Pupil reactions | normal | string |
| | 89 | Pupil reactions | moderate | string |
| 30 | 90 | Pupil reactions | inadequate | string |
| | 91 | Pupil reactions | absent | string |
| | 92 | Range of Motion grade | excessive | string |
| | 93 | Range of Motion grade | adequate | string |
| | 94 | Range of Motion grade | reduced | string |
| 35 | 95 | Range of Motion grade | mild | string |
| | 96 | Range of Motion grade | none | string |
| | 97 | Restrictions in looking behind | free | string |
| | 98 | Restrictions in looking behind | trunk stiffness | string |
| | 99 | Restrictions in looking behind | neck stiffness | string |
| 40 | 100 | Restrictions in looking behind | trunk & neck stiffness | string |
| | 101 | Right/Left ratio of the support | Right only | string |
| | 102 | Right/Left ratio of the support | much more | string |
| | 103 | Right/Left ratio of the support | moderate more | string |
| | 104 | Right/Left ratio of the support | more a little | string |
| 45 | 105 | Right/Left ratio of the support | near equal | string |
| | 106 | Right/Left ratio of the support | less a little | string |
| | 107 | Right/Left ratio of the support | moderate less | string |
| | 108 | Right/Left ratio of the support | essentially less | string |
| | 109 | Right/Left ratio of the support | Left only | string |

|    |     |               |           |        |
|----|-----|---------------|-----------|--------|
|    | 110 | Scoliosis     | absent    | string |
|    | 111 | Scoliosis     | mild      | string |
|    | 112 | Scoliosis     | moderate  | string |
|    | 113 | Scoliosis     | severe    | string |
| 5  | 114 | Stoop         | absent    | string |
|    | 115 | Stoop         | mild      | string |
|    | 116 | Stoop         | moderate  | string |
|    | 117 | Stoop         | severe    | string |
|    | 118 | Support grade | none      | string |
| 10 | 119 | Support grade | touch     | string |
|    | 120 | Support grade | slight    | string |
|    | 121 | Support grade | moderate  | string |
|    | 122 | Support grade | full      | string |
|    | 123 | Trunk bending | excessive | string |
| 15 | 124 | Trunk bending | adequate  | string |
|    | 125 | Trunk bending | reduced   | string |
|    | 126 | Trunk bending | mild      | string |
|    | 127 | Trunk bending | none      | string |
|    | 128 | Trunk twisting| excessive | string |
| 20 | 129 | Trunk twisting| adequate  | string |
|    | 130 | Trunk twisting| reduced   | string |
|    | 131 | Trunk twisting| mild      | string |
|    | 132 | Trunk twisting| none      | string |

25

WO 01/88836                                                              PCT/US01/16180

APPENDIX E

COMPOSITE RESULTS

| ID | Name |
|----|------|
| 1  | Null |
| 2  | Balancing strategies |
| 3  | Causes of a task failure |
| 4  | Gait patterns |
| 5  | Gazing features |
| 6  | Instability signs |
| 7  | Manner of Going around |
| 8  | Manner of a Turn 180□ |
| 9  | Orthopaedic aid |
| 10 | Side involved |
| 11 | Walking disorders |

COMPOSITE FEATURES

| ID | Name | Composite Results |
|----|------|-------------------|
| 1  | feet strategy | Balancing strategies |
| 2  | hip strategy | Balancing strategies |
| 3  | rescue reactions | Balancing strategies |
| 4  | stepping strategy | Balancing strategies |
| 5  | prevention reactions | Balancing strategies |
| 6  | none | Balancing strategies |
| 10 | musculoskeletal restriction | Causes of a task failure |
| 11 | instability | Causes of a task failure |
| 12 | fear | Causes of a task failure |
| 13 | refusal | Causes of a task failure |
| 14 | contraindicated | Causes of a task failure |
| 15 | others | Causes of a task failure |
| 20 | healthy elderly | Gait patterns |
| 21 | cautious gait | Gait patterns |
| 22 | senile gait | Gait patterns |
| 23 | limp | Gait patterns |
| 24 | festinating gait | Gait patterns |
| 25 | hysterical gait | Gait patterns |
| 26 | helicopod | Gait patterns |
| 27 | dysrhythmia | Gait patterns |
| 28 | parkinsonian | Gait patterns |
| 29 | paraplegic gait | Gait patterns |
| 30 | hemiplegic gait | Gait patterns |
| 31 | scissors | Gait patterns |
| 32 | freezing | Gait patterns |
| 33 | waddling | Gait patterns |
| 34 | veering | Gait patterns |
| 35 | antalgic | Gait patterns |
| 36 | ataxic/staggering/topple | Gait patterns |

|     |     |                              |                       |
| --- | --- | ---------------------------- | --------------------- |
|     | 37  | isolated gait ignition failure | Gait patterns       |
|     | 38  | abasia                       | Gait patterns         |
|     | 39  | apraxia                      | Gait patterns         |
|     | 50  | stable gazing                | Gazing features       |
| 5   | 51  | wandering glance             | Gazing features       |
|     | 52  | bizarre looking at           | Gazing features       |
|     | 53  | glance head asynergia        | Gazing features       |
|     | 54  | stopping in order to gaze    | Gazing features       |
|     | 60  | none                         | Instability signs     |
| 10  | 61  | rescue reactions             | Instability signs     |
|     | 62  | stepping strategy            | Instability signs     |
|     | 63  | prevention reactions         | Instability signs     |
|     | 64  | dizziness                    | Instability signs     |
|     | 65  | drop attack                  | Instability signs     |
| 15  | 70  | sagittal stepping            | Manner of Going around |
|     | 71  | lateral stepping             | Manner of Going around |
|     | 72  | with support                 | Manner of Going around |
|     | 73  | sagittal stepping            | Manner of Turn 180□   |
|     | 74  | lateral stepping             | Manner of Turn 180□   |
| 20  | 75  | with support                 | Manner of Turn 180□   |
|     | 80  | none                         | Orthopaedic aid       |
|     | 81  | AFO                          | Orthopaedic aid       |
|     | 82  | shoes                        | Orthopaedic aid       |
|     | 83  | orthosis                     | Orthopaedic aid       |
| 25  | 84  | below knee prosthesis        | Orthopaedic aid       |
|     | 85  | above knee prosthesis        | Orthopaedic aid       |
|     | 86  | cane                         | Orthopaedic aid       |
|     | 87  | crutches                     | Orthopaedic aid       |
|     | 88  | walker                       | Orthopaedic aid       |
| 30  | 100 | none                         | Side involved         |
|     | 101 | right                        | Side involved         |
|     | 102 | left                         | Side involved         |
|     | 103 | both                         | Side involved         |
|     | 110 | none                         | Walking disorders     |
| 35  | 111 | peroneal gait                | Walking disorders     |
|     | 112 | stamping                     | Walking disorders     |
|     | 113 | foot slap                    | Walking disorders     |
|     | 114 | dragging toe                 | Walking disorders     |
|     | 115 | crouch gait                  | Walking disorders     |
| 40  | 116 | calcaneal gait               | Walking disorders     |
|     | 117 | talipes equinus gait         | Walking disorders     |
|     | 118 | talipes equino-varus gait    | Walking disorders     |
|     | 119 | pigeon-toed gait             | Walking disorders     |
|     | 120 | inadequate shock absorbtion  | Walking disorders     |
| 45  | 121 | gluteus maximus weakness     | Walking disorders     |
|     | 122 | gluteus medius weakness      | Walking disorders     |
|     | 123 | pain at Init. Contact and in Stance | Walking disorders |

What is claimed is:

1. A method of processing video image data, the method comprising the steps of:

generating, based on the video image data, a plurality of silhouettes of a figure represented in the video image data;

forming a plurality of matrices, each matrix representing a silhouette in a frame of the video image data;

establishing a motion portrait from the plurality of matrices and based on the plurality of silhouettes; and calculating motion characteristics from the plurality of matrices and based on the plurality of silhouettes, wherein the motion characteristics are used to medically diagnose the figure represented in the video image data.

2. A method of measuring physiological characteristics of an individual with respect to movement of said individual comprising, in combination, the steps of:

video recording the individual performing a predefined routine of physical tasks;

processing, without human intervention, the video image recorded to define a silhouette pattern of the individual movement;

comparing the silhouette pattern with a standard;

determining the deviation of the silhouette pattern from the standard and determining whether at least one physiological characteristic is outside an expected normal range.

3. The method of claim 2 wherein the standard is a normalized representative sample for the predefined routine.

4. The method of claim 2 wherein the standard is an historic recording of the individual.

5. The method of claims 3 or 4 further including a sensor to detect a deviation from the standard.

6. The method of claim 5 wherein the deviation exceeds a limit and a sensor is provided to detect the exceeded limit.

7. The method of claim 6 wherein the deviation is announced.

8. The method of claim 2 wherein the predefined routine comprises walking from a side profile.

9. The method of claim 2 wherein the predefined routine comprises conduct of an arm motion protocol.

10. The method of claim 2 wherein the predefined routine comprises conduct of a head motion protocol.

11. The method of claim 2 wherein the predefined routine comprises a leg motion protocol.

12. The method of claim 2 wherein the predefined routine is recorded from the backside of the individual.

13. The method of claim 2 wherein the video image is recorded and stored.

14. A method for performing medical diagnosis based on physical motion of an individual conducted pursuant to a pre-defined protocol, comprising, in combination, the steps of:

positioning the individual in a field;

causing the individual to move in accord with an instruction;

video recording the individual movement from a fixed position;

processing, without human intervention, the video image of the individual to highlight the silhouette of the individual; and in response to the step of analyzing, determining whether the individual movement is associated with an expected normal range.

analyzing the modification of the video image by comparing the modification to a standard and in response to the step of analyzing, determining whether the individual movement is associated with an expected normal range.

15. The method of claim 2 or 14 including the step of performing a plurality of recordings of the individual, each recording constituting distinct pattern or routine.

16. The method of claim 15 wherein the patterns or routines are of varied difficulty.

17. The method of claim 15 wherein the patterns or routines are of increasing difficulty.

18. The method of claim 15 wherein the routine or pattern is varied quantitatively.

19. The method of claim 15 wherein the routine or pattern is varied qualitatively.

20. The method of claim 2 wherein the tasks are grouped as a collection of at least two sets of tests and wherein at least one task from at least two sets is conducted with an individual during a single recording session.

21. The method of claim 2 or 14 wherein at least one qualitative measurement is conducted during a single video recording session.

22. The method of claim 2 including the step of recording at least one qualitative measurement for each task.

23. The method of claim 2 or 14 including the step of recording at least one qualitative measurement.

24. The method of claim 1, 3 or 14 using a single video image source.

25. The method of claim 3, further comprising the step of:

ordering the plurality of separate tasks by associated levels of difficulty, wherein the step of instructing the entity is based upon the step of ordering.

26. The method of claim 1, further comprising the steps of:

saving the plurality of matrices as a data structure; and retrieving the data structure to obtain the plurality of matrices.

27. The method of claim 1, further comprising:

summing the plurality of matrices to form a graphical fingerprint, the graphical fingerprint providing a unique characteristic template of a patient, the patient corresponding to the figure.

* * * * *